(12) United States Patent
Stegemann et al.

(10) Patent No.: US 7,904,158 B2
(45) Date of Patent: Mar. 8, 2011

(54) MEASUREMENT OF CORONARY SINUS PARAMETERS TO OPTIMIZE LEFT VENTRICULAR PERFORMANCE

(75) Inventors: Berthold Stegemann, Aachen (DE); Rogier Receveur, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 1584 days.

(21) Appl. No.: 11/116,876

(22) Filed: Apr. 28, 2005

(65) Prior Publication Data

US 2006/0247702 A1    Nov. 2, 2006

(51) Int. Cl.
*A61N 1/00*    (2006.01)
(52) U.S. Cl. .......................................................... 607/18
(58) Field of Classification Search .................. 600/513, 600/364; 607/17–18, 22
See application file for complete search history.

(56) References Cited

U.S. PATENT DOCUMENTS

| | | |
|---|---|---|
| 3,358,690 A | 12/1967 | Cohen |
| 3,857,399 A | 12/1974 | Zacouto |
| 4,407,296 A | 10/1983 | Anderson |
| 4,432,372 A | 2/1984 | Monroe |
| 4,485,813 A | 12/1984 | Anderson et al. |
| 4,566,456 A | 1/1986 | Koning et al. |
| 4,774,950 A | 10/1988 | Cohen |
| 4,899,751 A | 2/1990 | Cohen |
| 4,899,752 A | 2/1990 | Cohen |
| 5,129,394 A | 7/1992 | Mehra |
| 5,158,078 A | 10/1992 | Bennett et al. |
| 5,213,098 A | 5/1993 | Bennett et al. |
| 5,224,475 A | 7/1993 | Berg et al. |
| 5,226,513 A | 7/1993 | Shibayama |
| 5,314,448 A | 5/1994 | Kroll et al. |
| 5,318,593 A | 6/1994 | Duggan |
| 5,336,244 A | 8/1994 | Weijand |
| 5,366,485 A | 11/1994 | Kroll et al. |
| 5,713,924 A | 2/1998 | Min et al. |

(Continued)

FOREIGN PATENT DOCUMENTS

EP    1386637 A1    4/2004

(Continued)

OTHER PUBLICATIONS

Olson et al. "Automatic Detection of Ventricular Fibrillation with Chronic Pressure Sensors", (abstract) JACC, vol. 7, No. 2, Feb. 1986, p. 182A.

(Continued)

*Primary Examiner* — Niketa I Patel
*Assistant Examiner* — Rex Holmes
(74) *Attorney, Agent, or Firm* — Stephen W. Bauer; Reed A. Duthler

(57) ABSTRACT

In some embodiments, an implantable medical device (IMD) system may include one or more of the following elements: (a) an oxygen sensor for measuring oxygen extraction from blood flowing through a coronary sinus of a patient's heart, (b) an oxygen signal generated by the oxygen sensor, (c) an IMD coupled to the oxygen sensor, wherein the IMD is configured to output pacing pulses as a function of the oxygen signal, and (d) an atrial and a ventricular pacing lead coupled to the IMD to deliver the pacing pulses to the patient's heart, wherein the IMD generates the pacing pulses as a function of the oxygen signal, wherein the pacing pulses are adjusted by the IMD as a function of the oxygen signal, wherein the IMD is configured to adjust the pacing pulses to increase oxygen in the blood flow through the coronary sinus.

10 Claims, 13 Drawing Sheets

U.S. PATENT DOCUMENTS

| | | | |
|---|---|---|---|
| 5,835,975 | A | 11/1998 | Peeters et al. |
| 6,666,821 | B2 | 12/2003 | Keimel |
| 6,754,532 | B1 | 6/2004 | Ferek-Petric |
| 7,389,142 | B2 * | 6/2008 | Holmstrom ............ 607/18 |
| 2003/0125774 | A1 | 7/2003 | Salo |
| 2003/0199957 | A1 | 10/2003 | Struble et al. |
| 2004/0077962 | A1 * | 4/2004 | Kroll ............... 600/513 |
| 2005/0075675 | A1 | 4/2005 | Mulligan et al. |

FOREIGN PATENT DOCUMENTS

| | | |
|---|---|---|
| WO | WO8701947 | 4/1987 |
| WO | WO2005000092 A2 | 1/2005 |

OTHER PUBLICATIONS

Cohen, "A Theoretical Right Atrial Pressure Feedback heart Rate Control System to Restore Physiologic Control to a Rate Limited Heart", PACE, vol. 7, pp. 671-677, Jul.-Aug. 1984.

* cited by examiner

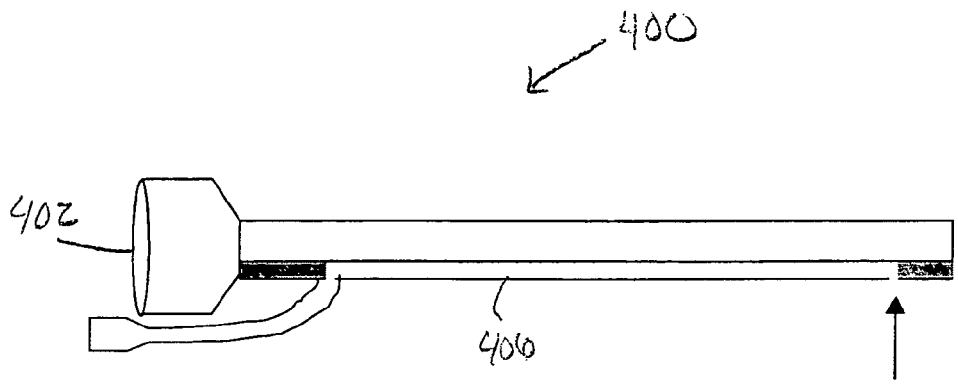
Fig. 6A   Blood sampling port
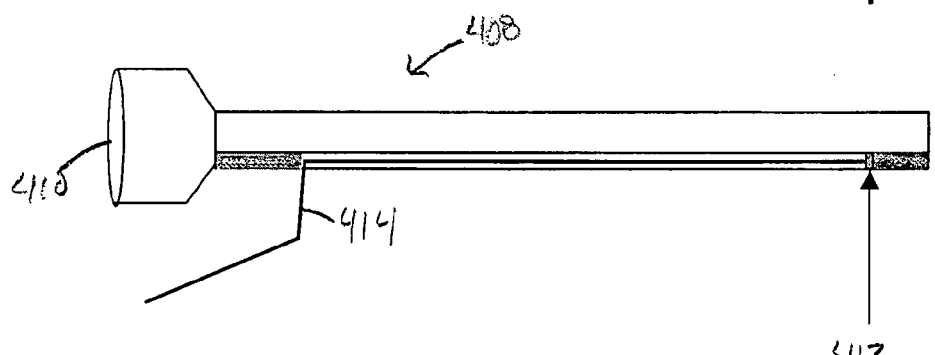
Fig. 6B   Biochemical sensors
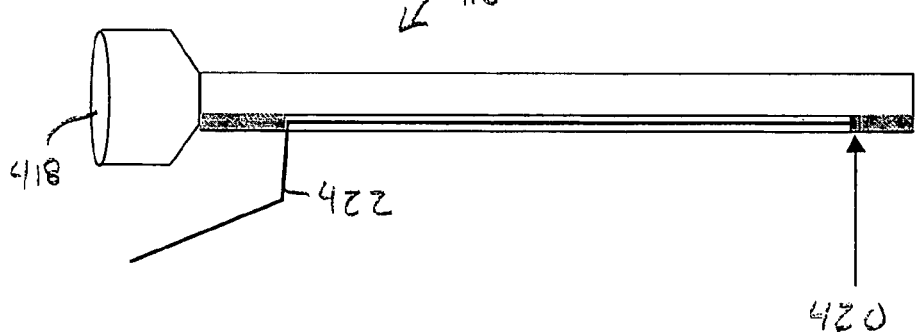
Fig. 6C   Pressure sensors

MEASUREMENT OF CORONARY SINUS PARAMETERS TO OPTIMIZE LEFT VENTRICULAR PERFORMANCE

FIELD

The present invention relates to a method and apparatus for measuring parameters within the coronary sinus and employing those parameters to control therapy delivery of a device in response to the physiologic needs of the cardiovascular system and trigger the delivery of an appropriate therapy, such as anti-tachyarrhythmia pacing, cardioversion, or defibrillation.

BACKGROUND

Advances in the treatment of bradyarrhythmias (slow heart beat) and tachyarrhythmias (fast heart beat) with implanted devices capable of detecting each condition and providing the appropriate therapy resulted in numerous advances in the art since simple fixed rate pacemakers were first implanted about thirty years ago. The control of the heart's rhythm by monitoring both electrical and mechanical heart function has been a goal of researchers in the field over that same period of time. For example, the 1961 pamphlet by Dr. Fred Zacouto, Paris, France, "Traitement D'Urgence des Differents Types de Syncopes Cardiaques du Syndrome de Morgangni-Adams-Stokes", (National Library of Medicine), describes an automatic pacemaker and defibrillator responsive to the presence or absence of the patient's blood pressure in conjunction with the rate of the patient's electrocardiogram. Very generally, a simple algorithm employing the patient's heart rate as evidenced by the electrical R-waves and the patient's blood pressure pulse was employed to: (1) operate a pacemaker pulse generator at a fixed rate in the presence of both signals recurring at less than a minimum rate or escape interval; (2) trigger the delivery of a defibrillation shock to the heart in the presence of a heart rate exceeding a tachyarrhythmia detect upper rate threshold in conjunction with the absence of a blood pressure signal over a variable period (such as thirty seconds); and, (3) inhibit both the pacemaker and defibrillator in the presence of both R-waves and blood pressure pulses recurring at a frequency exceeding the lower rate threshold but falling below the tachyarrhythmia detect threshold. It was long recognized earlier in medicine that the patient's blood pressure and electrocardiogram constituted the two most familiar and direct diagnostic tools for assessing the condition of the patient's cardiovascular system.

In this regard, it was also recognized early in the history of cardiac pacing that a patient dependent upon fixed rate pacing stimulation suffered cardiovascular insufficiency as his heart was able to increase its output (cardiac output) by only a limited amount in response to physiologic need. In normal hearts, the cardiovascular system responds to physiologic need by increasing both the heartbeat rate and its volume and systolic pressure (thereby increasing stroke volume and cardiac output) in response to physiologic need and as the heartbeat rate is limited in the pacing dependent patient to the fixed pacer rate, the heart's blood pressure and volume could increase proportional to physiologic need only to a limited extent. Thus, it was suggested by Juhasz in his 1965 article "Development of Implanted Cardiac Pacemakers", Digest of 6th Int'l Conf. on Medical Electrics and Biological Engineering, 1965, Tokyo, pp. 85-86, that blood pressure, among other parameters of the cardiovascular system, could be used as a forward transfer control value to vary pacing rates as a function of the blood pressure value, thus releasing the heart from the constraint imposed by the fixed base or lower pacing rate and allowing it to beat up to the pulse generator's upper pacing rate limit.

These early researchers were followed by numerous examples of the use of pressure signals of one form or another to control pacing rate or verify the presence of a tachyarrhythmia and trigger the delivery of appropriate therapies. For example, it has been proposed to sense pressure in the right atrium and to utilize a signal derived therefrom to affect and control right ventricular pacing as disclosed in Cohen U.S. Pat. No. 3,358,690. In addition, the Zacouto U.S. Pat. No. 3,857,399 (FIG. 19) discloses a pressure sensor on an extension of a pacing lead adapted to be forced into or through the ventricular septum to measure the intramyocardial pressure within the septum, and/or the actual left ventricular pressure. The signal derived from one or both of these sensors represents an average or mean pressure that varies over relatively long periods of time in a manner similar to that described in the Kresh PCT Publication No. WO87/01947. More recently, the publication of Todd J. Cohen, entitled "A Theoretical Right Atrial Pressure Feedback Heart Rate Control System to Restore Physiologic Control to a Rate Limited Heart", PACE, Vol. 7, pp. 671-677, July-August, 1984, discloses a system for comparing the mean right atrial pressure signal with a baseline signal and developing an error signal which, after processing, is used to control the pacing rate.

In addition, the microprocessor based implantable pacemaker and ventricular pressure sensing lead disclosed in Koning et al, U.S. Pat. No. 4,566,456, relates to right ventricular systolic pressure, the gross rate of change over time of the pressure ($\Delta.P/\Delta.t$) and/or the time derivative (dP/dt) of the systolic pressure with the rate needed to produce the desired cardiac output. Koning, in one algorithm, detects the right ventricular systolic pressure peak valves, averages N peak values and compares the current average to the preceding stored average value to detect the change in average pressure over time ($\Delta P/\Delta t$). That signal is employed to "look up" a $\Delta R$ or pacing rate change used to modify the pacing rate R.

More recently, Cohen U.S. Pat. No. 4,899,751 discloses a pacing system relying on a pressure signal from a pressure sensor located in the cardiovascular system, including the four chambers of the heart, coupled with signal processing circuitry for developing short term and long term mean (or average) pressure related control signals therefrom. The escape interval or rate of the pacemaker is controlled as a function of the difference between the short term and long term mean pressure values. Cohen, U.S. Pat. No. 4,899,752, provides a somewhat different algorithm in that the current mean pressure values are compared against fixed threshold values and the difference is employed to modify the pacing rate.

Medtronic U.S. Pat. Nos. 4,407,296, 4,432,372 and 4,485,813 describe various transvenous pressure sensors with associated pacing electrodes adapted to be positioned in a heart chamber to develop pressure values to control the operation of rate responsive pacemakers or to detect pathologic tachyarrhythmias and trigger the delivery of appropriate therapies.

In regard to the use of a blood pressure related signal detected within a heart chamber to confirm the detection of a tachyarrhythmia and trigger the delivery of an appropriate therapy, the initial system proposed by Mirowski et al in U.S. Pat. No. Re 27,757 relied upon the decrease in the amplitude of a pulsatile (systolic) right ventricular pressure signal below a threshold over a predetermined period of time ($\Delta P/\Delta t$) to commence the charging of a high energy output capacitor and deliver a shock to the heart if the pressure signal did not increase above the threshold during the charging time. The short lived pressure sensor available to Mirowski at that time was abandoned in favor of electrocardiogram rate and morphology detection.

More recently, the use of intramyocardial pressure and left ventricular pressure has been explored by a research group from Belgium (see, for example, the paper by Denys et al entitled "Ventricular Defibrillation Detection by Intramyocardial Pressure Gradients" in PROCEEDINGS OF THE SEVENTH WORLD SYMPOSIUM ON CARDIAC PACING, pp. 821-826, Verlag, 1983, and subsequent papers, such as "Automatic Defibrillator, Antitachy Pacemaker and Cardioverter", COMPUTERS AND CARDIOLOGY, IEEE COMPUTER SOCIETY PRESS, pp. 45-48, Oct. 7-10, 1986, and other papers by this group. This group has advocated the use of left ventricular impedance or pressure or a left ventricular pressure related signal over right ventricular pressure, and they resorted to use of ventricular intramyocardial pressure because of the difficulty of directly measuring pressure in the left ventricle and atrium.

In addition, a Japanese group has published papers such as "Design for an Implantable Defibrillator Using a Novel Heartbeat Sensor", Japanese Journal of Medical and Biological Engineering, 1984, pp. 43-48, by Makino et al. The Japanese group's sensor detects the pressure in the right ventricle using a catheter born electrode, or microphone, heartbeat sensor. The absence of a heartbeat for 3.5 seconds causes the fibrillation detector to switch the high voltage converter into operation.

The comparison of a current average pressure value to a longer term average control value derived from the heart during normal sinus rhythm to detect ventricular arrhythmias and trigger cardioversion/defibrillation therapies in response to a significant decrease in the current value was proposed by Olson et al, in "Automatic Detection of Ventricular Fibrillation with Chronic Pressure Sensors", (abstract), JACC, Vol. 7, No. 2, February, 1986, p. 182A.

More recently Cohen, U.S. Pat. No. 4,774,950, describes a system employing mean pressure values from any of the four chambers of the heart representative of the long-term mean base line pressure and the short-term current mean pressure to indicate or confirm the indication of a tachyarrhythmia and to trigger cardioversion/defibrillation shock therapies when the difference between the two mean pressure values exceeds a predetermined threshold value.

It has been thought that the truest indication of the degree of hemodynamic compromise of the malfunctioning heart is the left ventricular pressure which is measurable only with some difficulty. For example, Zacouto, Kresh, the Belgian group and Cohen (in the '751 and '950 patents) all have sought in one way or another to determine the left ventricular pressure by locating a pressure sensor within the left ventricle or within the myocardial tissue. Placing and retaining a pressure sensor in either location involves some risk that the high pressure, left ventricular chamber will be breached at the point of penetration causing the patient to hemorrhage as expressly commented on by the Belgian group. Thus with current technology, it is undesirable to so situate a pressure sensing transducer.

SUMMARY

In some embodiments, medical device systems include one or more of the following elements: (a) an oxygen sensor for measuring oxygen extraction from blood flowing through a coronary sinus of a patient's heart, (b) an oxygen signal generated by the oxygen sensor, (c) an implantable medical device (IMD) coupled to the oxygen sensor, wherein the IMD is configured to output pacing pulses as a function of the oxygen signal, (d) an atrial and a ventricular pacing lead coupled to the IMD to deliver the pacing pulses to the patient's heart, wherein the IMD generates the pacing pulses as a function of the oxygen signal, wherein the pacing pulses are adjusted by the IMD as a function of the oxygen signal, wherein the IMD is configured to adjust the pacing pulses to increase oxygen in the blood flow through the coronary sinus, (e) a blood pressure sensor for detecting a signal proportional to the left heart chamber blood pressure, (f) a blood flow sensor for measuring coronary blood flow producing a blood flow signal, (g) a glucose sensor for sensing a rate of extraction of glucose through the coronary sinus and producing a glucose signal, and (h) a blood temperature sensor for sensing the temperature of the blood in the coronary sinus and producing a temperature signal.

In some embodiments, a method for pacing a patient's heart using an IMD includes one or more of the following steps: (a) sensing a rate extraction of glucose through a coronary sinus of a patient's heart, (b) generating a pacing pulse as a function of the sensed rate, (c) adjusting a pacing parameter of the pacing pulse as a function of a glucose signal, (d) adjusting the pacing parameter to optimize left ventricular performance, (e) adjusting the pacing parameter of the pacing pulse as a function of the glucose signal and a blood pressure signal produced by a blood pressure sensor for detecting a signal proportional to the left heart chamber blood pressure, (f) adjusting the pacing parameter of the pacing pulse as a function of the glucose signal and a blood flow signal produced by a blood flow sensor for measuring coronary blood flow, (g) adjusting the pacing parameter of the pacing pulse as a function of the glucose signal and an oxygen signal produced by an oxygen sensor for measuring oxygen extraction from blood flowing through a coronary sinus of a patient's heart, (h) adjusting the pacing parameter of the pacing pulse as a function of a glucose signal and a blood temperature signal produced by a blood temperature sensor for sensing the temperature of the blood in the coronary sinus, (i) adjusting the pacing parameter during implantation of the implantable medical device to optimize the delivery of the pacing pulses, and (j) adjusting the pacing parameter as the heart changes during the life of a patient.

In some embodiments, an implantable multi-chamber pacing system may include one or more of the following elements: (a) atrial sense means for sensing signals from an atrium of a patient's heart, (b) ventricular sense means for sending ventricular signals from a patient's right ventricle, (c) coronary sense means for sensing ventricular signals from the patient's left ventricle and for sensing a signal representing blood temperature through the patient's coronary sinus, (d) pace control means for generating and delivering pacing pulses to a plurality of chambers within the patient's heart, wherein the pace control means includes means for setting and timing cardiac resynchronization therapy as a function of the sensed temperature signal.

DRAWINGS

FIG. 6A is a diagram of lead delivery catheter blood sampling device in an embodiment of the present invention.

FIG. 6B is a diagram of lead delivery catheter having a biochemical sensor in an embodiment of the present invention.

FIG. 6C is a diagram of lead delivery catheter having a pressure sensor in an embodiment of the present invention.

DESCRIPTION OF VARIOUS EMBODIMENTS

Figure 1:
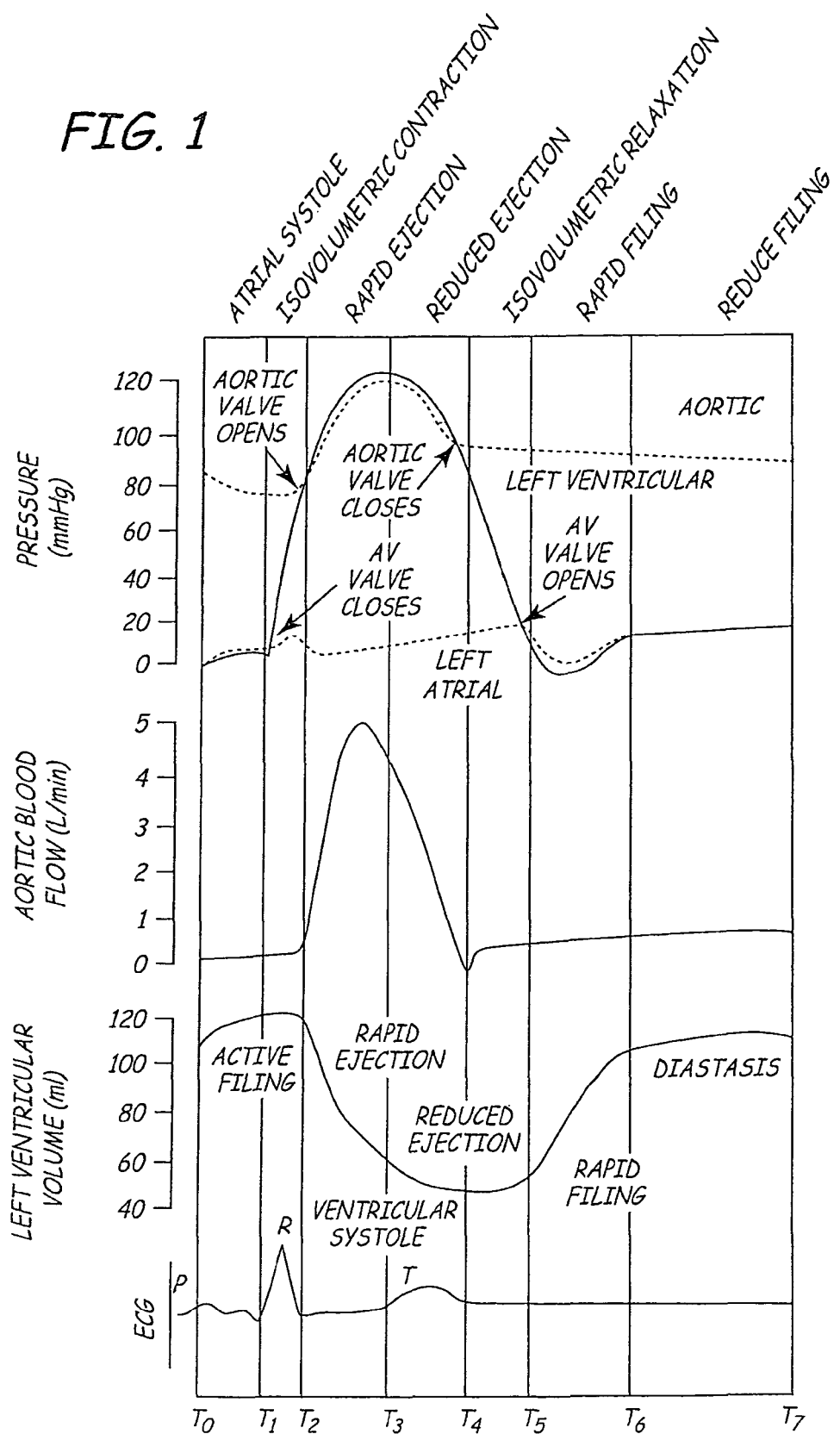
FIG. 1 depicts the relationship of heart chamber EGM, pressure, flow, and volume during a cardiac cycle.

The following discussion is presented to enable a person skilled in the art to make and use embodiments of the invention. Various modifications to the illustrated embodiments will be readily apparent to those skilled in the art, and the generic principles herein may be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention. The following introductory material is intended to familiarize the reader with the general nature and some of the features of embodiments of the invention.

A system constructed and operated according to embodiments of the invention that may be used to deliver the therapies discussed above may include a signal generator, timing circuit, and/or microprocessor control circuit of the type included in existing pacemaker or ICD systems as is known in the art. Exemplary systems are shown in U.S. Pat. Nos. 5,158, 078, 5,318,593, 5,226,513, 5,314,448, 5,366,485, 5,713,924, 5,224,475 and 5,835,975 each of which is incorporated herein by reference, although any other type of pacing and/or ICD system may be used for this purpose. In such systems, EGM sensing is performed by electrodes carried on leads placed within the chambers of the heart, and/or on the housing of the device. Alternatively, subcutaneous and/or external pad or patch electrodes may be used to sense cardiac signals. Physiological sensors may likewise be carried on lead systems according to any of the configurations and/or sensing systems known in the art.

The following introductory material is intended to familiarize the reader with the general nature and some of the features of embodiments of the invention.

All embodiments of the invention share a common need for electrode configurations to deliver electrical stimulation energy where necessary and to time the delivery of this energy to achieve beneficial effects while avoiding unsafe delivery. For each therapy component described above, specific electrode locations and geometries may be preferred. The locations for the electrodes of these teachings for stimulation include: use of large surface area defibrillation coil electrodes in the heart or adjacent to the heart; pacing electrodes at locations including RV apex, outflow tract, atrial locations, HIS bundle site, left side epicardium, pericardium or endocardium; transthoracic electrodes including paddles and patches, can electrode, temporary electrodes (e.g., epicardial, transvenous or post-operative electrodes), subcutaneous electrodes and multiple site stimulation.

In accordance with common biomedical engineering practices, stimulation therapy is applied with minimized net charge delivery to reduce corrosion and counteract polarization energy losses. Both energy efficient therapy delivery and electrogram (EGM) sensing benefit from low polarization lead systems. Finally, the electrodes are preferably connected to fast recovery amplifiers that allow EGM sensing soon after therapy delivery.

The most fundamental sensors are those based on electrograms (ECG or EGMs) and reflect cardiac electrical activity. These sensors require electrodes located where they can readily detect depolarization and repolarization signals as well as sense amplifiers for the monitoring of heart rhythm and diagnosis of arrhythmias.

According to one embodiment, blood pressure sensors, accelerometers, flow probes, microphones, or sonometric crystals may be used to measure flow, force, velocity, movement of the walls of the heart, and/or to estimate the volume of the cardiac chambers. Parameters derived from these sensors can also be used to detect the onset and severity of cardiac hemodynamic dysfunction. For example, HF decompensation may be indicated when a change in long-term diastolic cardiac pressure has increased while contractility of the heart derived from dP/dt rate of rise of ventricular pressure has diminished. Another embodiment of the invention may utilize changes in transthoracic or intracardiac impedance signals to sense cardiac motion and respiratory movement. Metabolic or chemical sensors such as expired $CO_2$ and blood oxygen saturation, pH, $pO_2$, and/or lactate may be employed to reflect cardiac dysfunction.

Other signals such as surface electrocardiogram (ECG) or electrogram (EGM) signals from electrodes within the patient's body may be used to detect dysfunction and heart failure (HF). For example, the ST segment level of a cardiac cycle (PQRST) detected by an ECG may be monitored. An elevated or depressed ST segment level has been found to be reliable indicator of ischemia, a condition known to be associated with dysfunction and HF. Alternatively, the duration of the Q-T interval may also be used to detect hemodynamic dysfunction. For example, a shortened Q-T interval may indicate myocardial dysfunction. A template-matching algorithm such as a wavelet classification algorithm may be used to identify electrogram signals that are associated with hemodynamic dysfunction.

Chemical sensors may be used to initiate therapy, including sensors that analyze the blood to detect changes in B-type Neurouretic Peptide (BNP), lactate, $O_2$ saturation, $PO_2$, $PCO_2$, neurohormones, and pH. Expired gas may be analyzed for $PCO_2$ as an indicator of cardiac output during resuscitation procedures. Pulse oximetry may provide noninvasive assessments of oxygen saturation and pulse plethysmogram signals.

Although pressure sensors figure prominently in the examples above, a number of other sensors could record or transduce mechanical function. Intracardiac or transthoracic impedance changes reflect mechanical function, stroke volume, and cardiac output. Accelerometers or microphones within the body or applied externally sense cardiac dysfunction and monitor the response to therapy. Heart volume, dimension changes, and velocities may be measured by implanted or external applications of ultrasound.

Physiologic signals may continue to be sensed to determine if a therapy termination condition is met so that therapy may be terminated. An additional aspect of embodiments of the invention is to include not only a mechanical sensor in or on the heart to detect cardiac function, but a second sensor or a multitude of sensors away from the heart, such as inside the implantable device housing or can (acting as an indifferent electrode). From this second sensor, CPR artifact (due to chest compressions and the like) could be identified and subtracted to reveal a more accurate assessment of true cardiac function.

FIG. 1 is provided as background information and illustrates the electrical depolarization waves attendant a normal sinus rhythm cardiac cycle in relation to the fluctuations in absolute blood pressure, aortic blood flow and ventricular volume in the left heart. The right atria and ventricles exhibit roughly similar pressure, flow, and volume fluctuations, in relation to the PQRST complex, as the left atria and ventricles. It is understood that the monitoring and stimulation therapy aspects of these teachings may reside and act on either or both sides of the heart. The cardiac cycle is completed in the interval between successive PQRST complexes and following relaxation of the atria and ventricles as the right and left atria re-fill with venous blood and oxygenated blood. In sinus rhythm, the interval between depolarizations may be on the order of 500.0 ms to 1,000.0 ms for a corresponding sinus heart rate of 120 bpm to 60 bpm, respectively. In this time interval, the atria and ventricles are relaxed, and overall atrial size or volume may vary as a function of pleural pressure and respiration. In the blood pressure diagrams of FIG. 1, it may be observed that the atrial and ventricular blood pressure changes track and lag the P-waves and R-waves of the cardiac cycle. The time period $T_0$-$T_1$ encompasses the AV interval.

In patients suffering from cardiac insufficiency arising from bradycardia due to an incompetent SA node or AV-block, atrial and/or ventricular conventional pacing may be prescribed to restore a sufficient heart rate and AV synchrony.

In FIG. 1 for example, atrial and/or ventricular pacing pulses would precede the P-wave and the deflection of the QRS complex commonly referred to as the R-wave. Cardiac output may be reduced by the inability of the atrial or ventricular myocardial cells to relax following atrial ($T_0$-$T_1$) and ventricular ($T_1$-$T_2$) systolic periods. Prolonged systolic time periods reduce passive filling time $T_4$-$T_7$ as shown in FIG. 1. Thus, the amount of blood expelled from the atria and/or ventricles in the next cardiac cycle may be less than optimum. This is particularly the case with HF patients or other patients in whom the stiffness of the heart is increased, cardiac filling during the passive filling phase (T4-$T_7$) and during atrial systole (T0-$T_1$) is significantly limited.

It will be appreciated from the following description that the monitor/therapy delivery IMD of embodiments of the invention may be utilized to obtain the aforementioned parameters as stored patient data over a period of time and to deliver therapies for treating the heart failure. The physician is able to initiate uplink telemetry of the patient data in order to review it to make an assessment of the heart failure state of the patient's heart. The physician can then determine whether a particular therapy is appropriate, prescribe the therapy for a period of time while again accumulating the stored patient data for a later review and assessment to determine whether the applied therapy is beneficial or not, thereby enabling periodic changes in therapy, if appropriate. Such therapies include drug therapies and electrical stimulation therapies, including PESP and/or NES stimulation, and pacing therapies including single chamber, dual chamber and multi-chamber (bi-atrial and/or bi-ventricular) pacing. Moreover, in patients prone to malignant tachyarrhythmias, the assessment of heart failure state can be taken into account in setting parameters of detection or classification of tachyarrhythmias and the therapies that are delivered.

Accordingly, an embodiment of the invention is disclosed in detail in the context of a multi-chamber pacing system that is modified to derive the aforementioned parameters indicative of cardiac mechanical dysfunction from sensors, sense electrodes and electrical stimulation electrodes located in operative relation to one or more heart chamber. This embodiment of the invention may be programmed to operate as an AV sequential, bi-atrial and bi-ventricular, pacing system operating in demand, atrial tracking, and triggered pacing for restoring synchrony in depolarizations and contraction of left and right ventricles in synchronization with atrial sensed and paced events for treating HF and/or bradycardia. This embodiment of the invention is therefore programmable to operate as a two, three or four channel pacing system having an AV synchronous operating mode for restoring upper and lower heart chamber synchronization and right and left atrial and/or ventricular chamber depolarization synchrony. However, it will be understood that only certain of the components of the complex multi-chamber pacing system described below can be selectively programmed to function or physically only incorporated into a simpler, single chamber, monitoring/stimulation system for deriving the parameters indicative of heart failure state.

Figure 2:
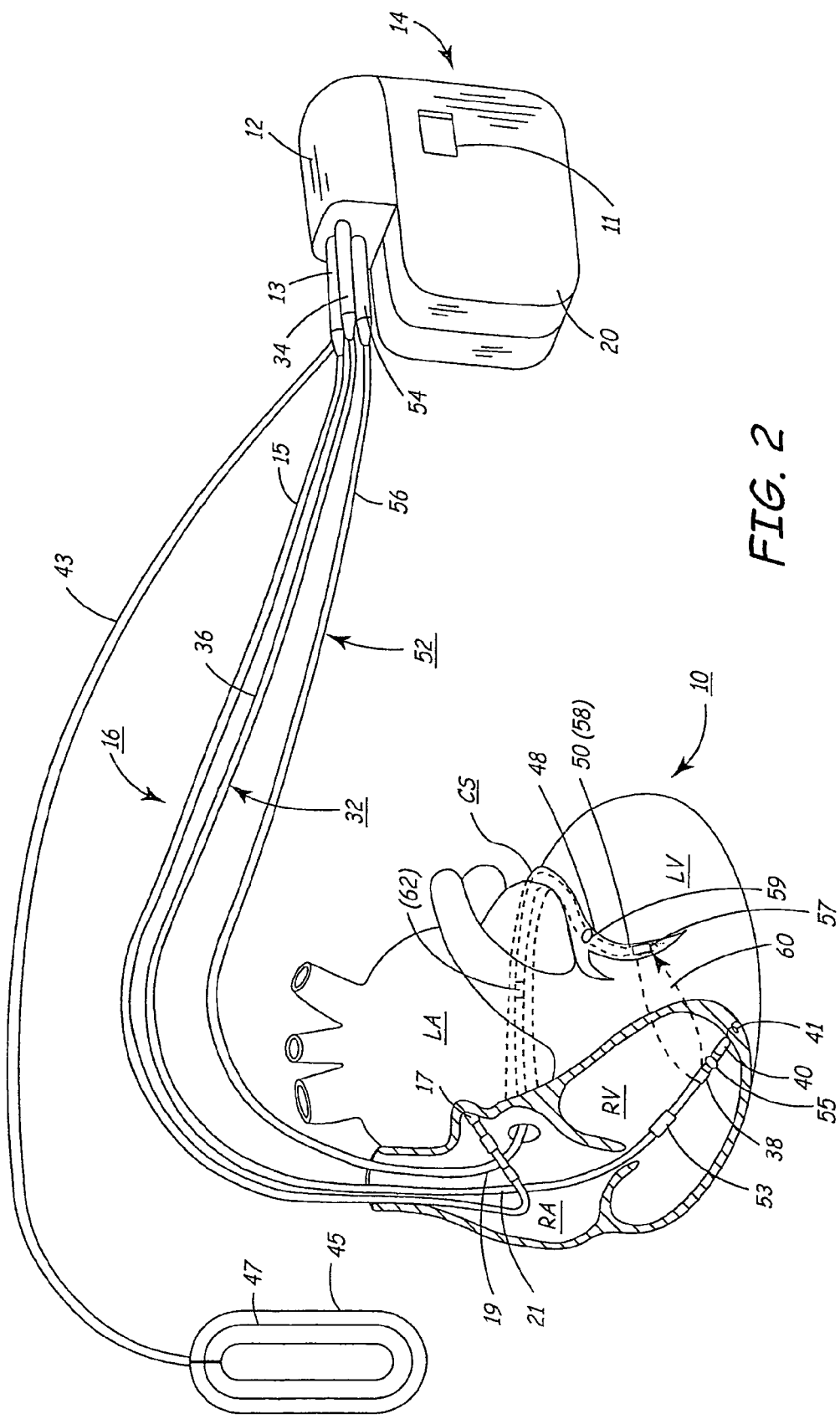
FIG. 2 is a schematic diagram depicting a multi-channel, atrial and bi-ventricular, monitoring/pacing IMD in which embodiments of the invention is preferably implemented.

In FIG. 2, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the great vein that extends further inferiority into branches of the great vein. The cardiac cycle commences normally with the generation of the depolarization impulse at the SA Node in the right atrial wall. The impulse then conducts through the right atrium by way of Internodal Tracts, and conducts to the left atrial septum by way of Bachmann's Bundle. The RA depolarization wave reaches the Atrio-ventricular (AV) node and the atrial septum within about 40 msec and reaches the furthest walls of the RA and LA within about 70 msec. Approximately 50 msec following electrical activation, the atria contract. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node conducts down the bundle of His in the intraventricular septum after a delay of about 120 msec. The depolarization wave reaches the apical region of the heart about 20 msec later and then travels superiorly though the Purkinje Fiber network over the remaining 40 msec. The aggregate RV and LV depolarization wave and the subsequent T-wave accompanying re-polarization of the depolarized myocardium are referred to as the QRST portion of the PQRST cardiac cycle complex when sensed across external ECG electrodes and displayed. When the amplitude of the QRS ventricular depolarization wave passing between a bipolar or unipolar pace/sense electrode pair located on or adjacent to the RV or LV exceeds a threshold amplitude, it is detected as a sensed R-wave. Although the location and spacing of the external ECG electrodes or implanted unipolar ventricular pace/sense electrodes has some influence on R-wave sensing, the normal R-wave duration does not exceed 80 msec as measured by a high impedance sense amplifier. A normal near field R-wave sensed between closely spaced bipolar pace/sense electrodes and located in or adjacent the RV or the LV has a width of no more than 60 msec as measured by a high impedance sense amplifier.

The normal electrical activation sequence becomes highly disrupted in patients suffering from advanced HF and exhibiting Intra-atrial and/or Inter-atrial conduction delay (IACD), Left Bundle Branch Block (LBBB), Right Bundle Branch Block (RBBB), Interventricular and/or Intraventricular Conduction Delay (IVCD). These conduction defects give rise to great asynchrony between RV activation and LV activation. Inter-ventricular asynchrony can range from 80 to 200 msec or longer. In RBBB and LBBB patients, the QRS complex is widened far beyond the normal range to between 120 msec and 250 msec as measured on surface ECG. This increased width demonstrates the lack of synchrony of the right and left ventricular depolarizations and contractions.

FIG. 2 also depicts an implanted, multi-channel cardiac pacemaker, ICD, IPG or other IMD of the above noted types for restoring AV synchronous contractions of the atrial and ventricular chambers and simultaneous or sequential pacing of the right and left ventricles. The pacemaker IPG 14 is implanted subcutaneously in a patient's body between the skin and the ribs. Three endocardial leads 16, 32, and 52 connect the IPG 14 with the RA, the RV, and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions. The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a unipolar, endocardial LV CS lead 52 is passed through a vein and the RA chamber of the heart 10, into the CS and then inferiority in a branching vessel of the great vein 48 to extend the distal LV CS pace/sense electrode 50 alongside the LV chamber. The distal end of such LV CS leads is advanced through the superior vena cava, the right atrium, the ostium of the coronary sinus, the coronary sinus, and into a coronary vein descending from the coronary sinus, such as the great vein. Typically, LV CS leads and LA CS leads do not employ any fixation mechanism and instead rely on the close confinement within these vessels to maintain the pace/sense electrode or electrodes at a desired site. The LV CS lead 52 is formed with a small diameter single conductor lead body 56 coupled at the proximal end connector 54 fitting into a bore of IPG connector block 12. A small diameter unipolar lead body 56 is selected in order to lodge the distal LV CS pace/sense electrode 50 deeply in a vein branching inferiority from the great vein 48.

In some embodiments, the distal, LV CS active pace/sense electrode 50 is paired with the proximal ring RV indifferent pace/sense electrode 38 for delivering LV pace pulses across the bulk of the left ventricle and the intraventricular septum. The distal LV CS active pace/sense electrode 50 is also preferably paired with the distal tip RV active pace/sense electrode 40 for sensing across the RV and LV as described further below. However, a true bipolar LV CS pace/sense can be used as well.

Moreover, in a four-chamber embodiment, LV CS lead 52 could bear a proximal LA CS pace/sense electrode positioned along the lead body to lay in the larger diameter coronary sinus CS adjacent the LA. In that case, the lead body 56 would encase two electrically insulated lead conductors extending proximally from the more proximal LA CS pace/sense electrode(s) and terminating in a bipolar connector 54. The LV CS lead body would be smaller between the proximal LA CS electrode and the distal LV CS active pace/sense electrode 50. In that case, pacing of the RA would be accomplished along the pacing vector between the active proximal LA CS active electrode and the proximal ring RA indifferent pace/sense electrode 21.

Typically, in pacing/defibrillation systems of the type illustrated in FIG. 2, the electrodes designated above as "pace/sense" electrodes are used for both pacing and sensing functions. In accordance with one aspect of embodiments of the invention, these "pace/sense" electrodes can be selected to be used exclusively as pace or sense electrodes or to be used in common as pace/sense electrodes in programmed combinations for sensing cardiac signals and delivering pace pulses along pacing and sensing vectors. Separate or shared indifferent pace and sense electrodes can also be designated in pacing and sensing functions. For convenience, the following description separately designates pace and sense electrode pairs where a distinction is appropriate. With respect to embodiments of the invention, a subcutaneous electrode 45 coupled to medical electrical lead 43 may be added to or substituted for one or more of the leads or electrodes depicted in FIG. 2. If a subcutaneous electrode 45 is utilized, a suitable defibrillation coil 47 may be coupled to appropriate high voltage circuitry to deliver a timed defibrillation pulse. While coil electrode 53 is depicted coupled to a portion of RV lead 32, such an electrode may be coupled to other portions of any of the leads depicted in FIG. 2, such as LV electrode 57. The coil electrode 53, subcutaneous electrode 45, or other types of suitable electrode configurations may be electrically coupled to low voltage pacing/sensing circuitry in addition to high voltage circuitry. As is known, such electrodes may be disposed in a variety of locations in, around, and on the heart.

Also depicted in FIG. 2 is an RV sensor 55 and an LV sensor 59 which may comprise one or more of a variety of sensors as is known in the art. Preferably RV sensor 55 comprises an absolute pressure sensor, but other pressure sensors may be utilized. In addition, RV sensor 55 may comprise an accelerometer, an impedance electrode, a saturated oxygen sensor, a pH sensor, and the like. In addition, each of the leads could carry a mechanical sensor for developing systolic and diastolic pressures and a series of spaced apart impedance sensing leads for developing volumetric measurements of the expansion and contraction of the RA, LA, RV and LV.

Of course, such sensors must be rendered biocompatible and reliable for long-term use. In addition, one or more sensors may be disposed in or on the housing 20 of IMD 14 such as sensor 11 depicted in FIG. 2.

Figure 3A:
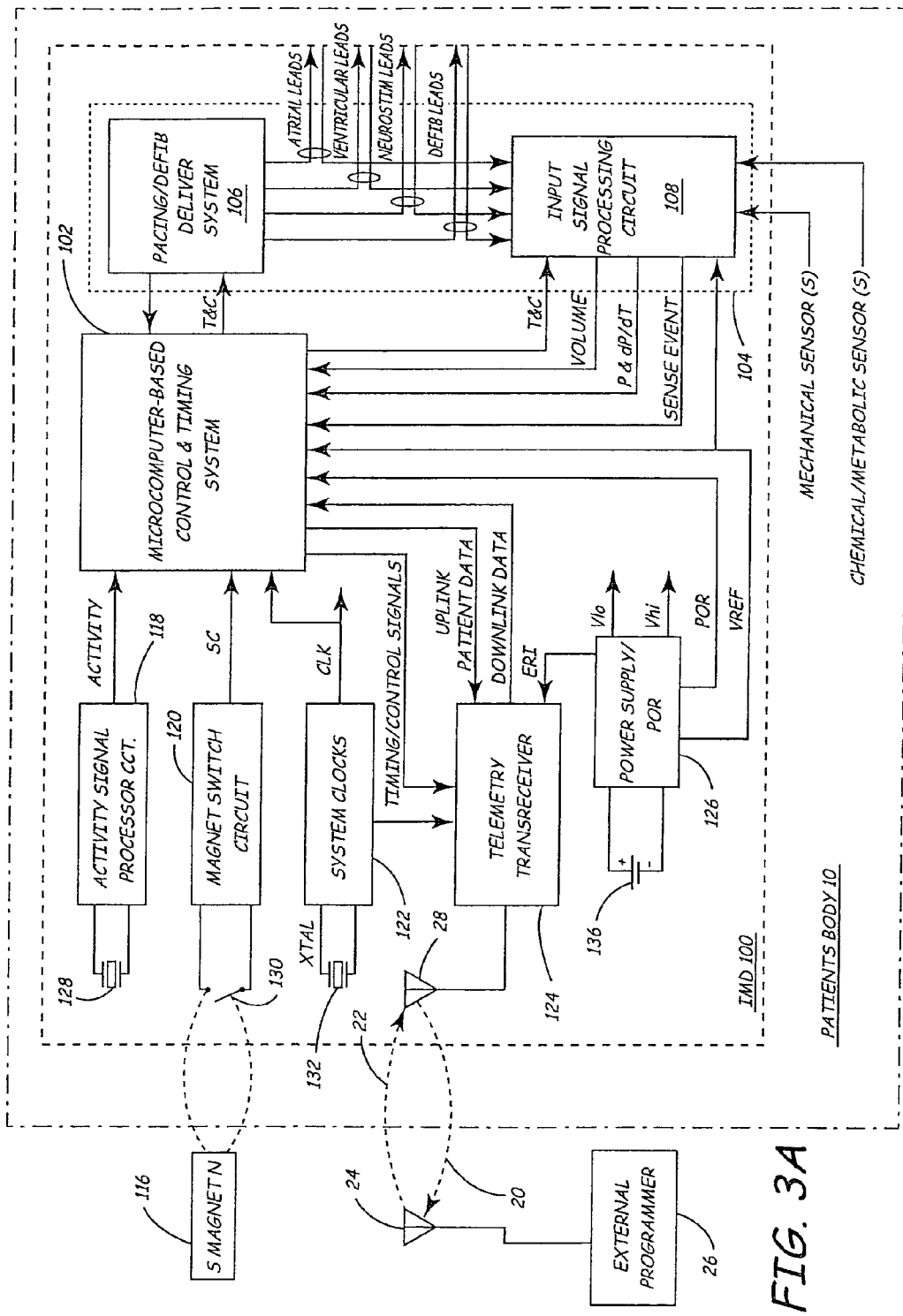
FIG. 3A is a simplified block diagram of one embodiment of IPG circuitry and associated leads employed in the system of FIG. 1 enabling selective therapy delivery and heart failure state monitoring in one or more heart chamber.

FIG. 3A depicts a system architecture of an exemplary multi-chamber monitor/sensor 100 implanted into a patient's body 10 that provides delivery of a therapy and/or physiologic input signal processing. The typical multi-chamber monitor/sensor 100 has a system architecture that is constructed about a microcomputer-based control and timing system 102 that varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU, ALU, etc., of a typical microprocessor core architecture. Of course, such firmware and software may be modified in situ (e.g., in vivo) and the operational characteristics may be adapted for a particular situation or patient. A physician or clinician may change one or more parameters, which will cause a change in the detection or response of such algorithms. Oftentimes, discrete values may be changed such that a desired software routine is advantageously altered, although sometimes an entirely new set of operating software may be substituted for an existing set of operating software, as is known in the art. The microcomputer-based multi-chamber monitor/sensor control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of multi-chamber monitor/sensor 100 can be accomplished with dedicated circuit hardware or state machine logic rather than a programmed microcomputer.

The multi-chamber monitor/sensor 100 also typically includes patient interface circuitry 104 for receiving signals from sensors and pace/sense electrodes located at specific sites of the patient's heart chambers and/or delivering stimulation to derive heart failure parameters or a pacing therapy to the heart chambers. The patient interface circuitry 104 therefore comprises a stimulation delivery system 106 optionally including pacing and other stimulation therapies and a physiologic input signal processing circuit 108 for processing the blood pressure and volumetric signals output by sensors. For purposes of illustration of the possible uses of embodiments of the invention, a set of lead connections are depicted for making electrical connections between the therapy delivery system 106 and the input signal processing circuit 108 and sets of pace/sense electrodes located in operative relation to the RA, LA, RV and LV.

As depicted in FIG. 3A, chemical/metabolic sensor input and/or mechanical sensor inputs are provided to the input signal processing circuit 108. As described with respect to FIG. 2, a wide variety of such sensors may be utilized when practicing embodiments of the invention. These sensors have been described above and are discussed below in more detail.

A battery provides a source of electrical energy to power the multi-chamber monitor/sensor operating system including the circuitry of multi-chamber monitor/sensor 100 and to power any electromechanical devices, or to provide electrical stimulation energy of an ICD shock generator, cardiac pacing pulse generator, or other electrical stimulation generator. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF sources, current sources, an elective replacement indicator (ERI) signal, and, in the case of an ICD, high voltage power Vhi to the therapy delivery system 106.

Virtually all current electronic multi-chamber monitor/sensor circuitry employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 3A, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers may be used for storing data compiled from sensed cardiac activity and/or relating to device operating history or sensed physiologic parameters for uplink telemetry transmission on receipt of a retrieval or interrogation instruction via a downlink telemetry transmission. The criteria for triggering data storage can also be programmed in via downlink telemetry transmitted instructions and parameter values The data storage is either triggered on a periodic basis or by detection logic within the physiologic input signal processing circuit 108 upon satisfaction of certain programmed-in event detection criteria. In some cases, the multi-chamber monitor/sensor 100 includes a magnetic field sensitive switch 130 that closes in response to a magnetic field, and the closure causes a magnetic switch circuit to issue a switch closed (SC) signal to control and timing system 102 which responds in a magnet mode. For example, the patient may be provided with a magnet 116 that can be applied over the subcutaneously implanted multi-chamber monitor/sensor 100 to close switch 130 and prompt the control and timing system to deliver a therapy and/or store physiologic episode data when the patient experiences certain symptoms. In either case, event related data, e.g., the date and time, may be stored along with the stored periodically collected or patient initiated physiologic data for uplink telemetry in a later interrogation session.

In the multi-chamber monitor/sensor 100, uplink and downlink telemetry capabilities are provided to enable communication with either a remotely located external medical device or a more proximal medical device on the patient's body or another multi-chamber monitor/sensor in the patient's body as described above with respect to FIG. 2 and FIG. 3A (and FIG. 3B described below). The stored physiologic data of the types described above as well as real-time generated physiologic data and non-physiologic data can be transmitted by uplink RF telemetry from the multi-chamber monitor/sensor 100 to the external programmer or other remote medical device 26 in response to a downlink telemetered interrogation command. The real-time physiologic data typically includes real time sampled signal levels, e.g., intracardiac electrocardiogram amplitude values, and sensor output signals. The non-physiologic patient data includes currently programmed device operating modes and parameter values, battery condition, device ID, patient ID, implantation dates, device programming history, real time event markers, and the like. In the context of implantable pacemakers and ids, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies. The multi-chamber monitor/sensor thus develops a variety of such real-time or stored, physiologic or non-physiologic, data, and such developed data is collectively referred to herein as "patient data".

The physiologic input signal processing circuit 108 therefore includes at least one electrical signal amplifier circuit for amplifying, processing and in some cases detecting sense events from characteristics of the electrical sense signal or sensor output signal. The physiologic input signal processing circuit 108 in multi-chamber monitor/sensors providing dual chamber or multi-site or multi-chamber monitoring and/or pacing functions includes a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave or R-wave, respectively and providing an ASENSE or VSENSE event signal to the control and timing system 102. Timing and control system 102 responds in accordance with its particular operating system to deliver or modify a pacing therapy, if appropriate, or to accumulate data for uplink telemetry transmission or to provide a Marker Channel® signal in a variety of ways known in the art.

In addition, the input signal processing circuit 108 includes at least one physiologic sensor signal-processing channel for sensing and processing a sensor derived signal from a physiologic sensor located in relation to a heart chamber or elsewhere in the body.

Figure 3B:
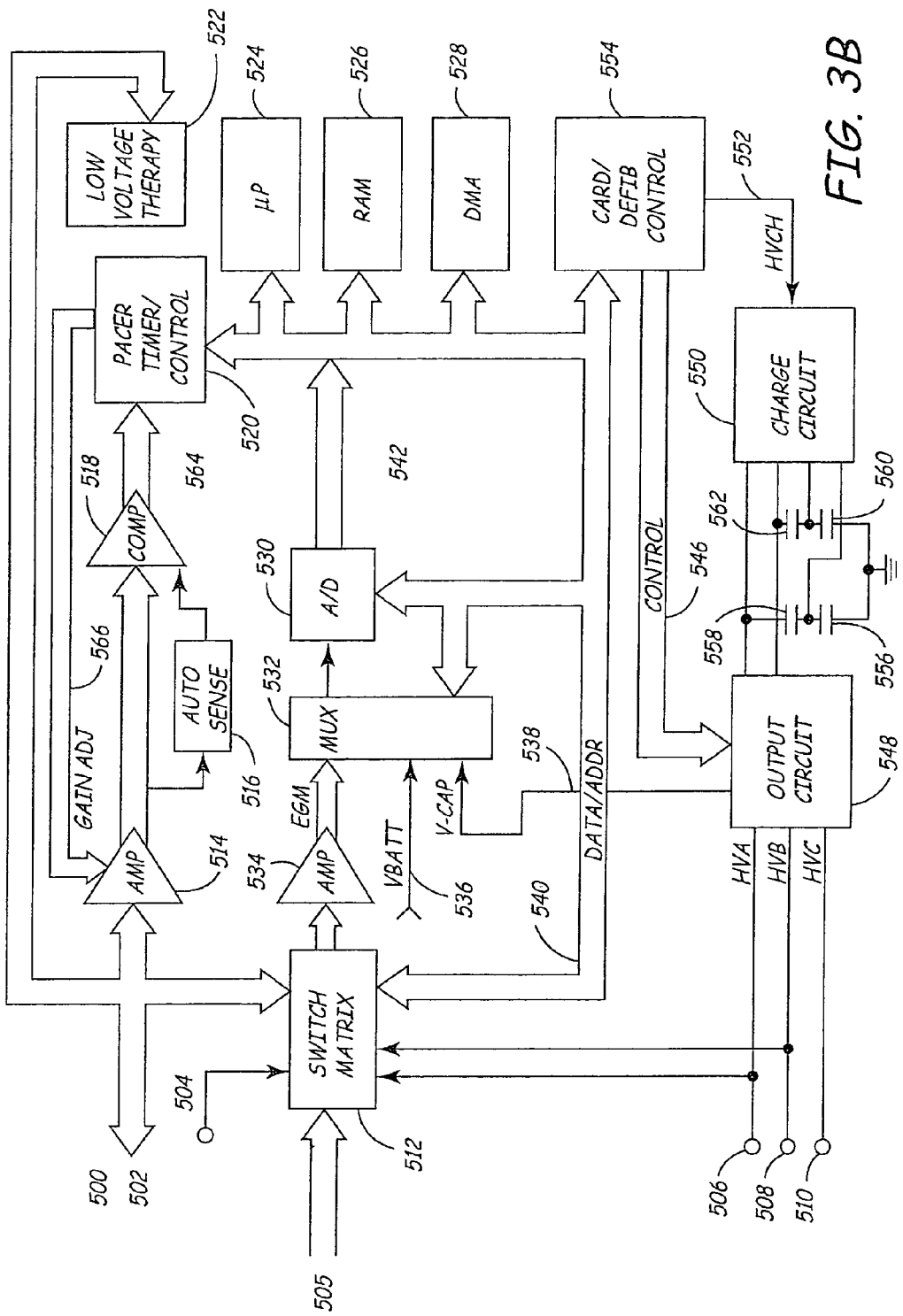
FIG. 3B is a simplified block diagram of another embodiment of IPG circuitry and associated leads employed in the system of FIG. 1 enabling selective therapy delivery and heart failure state monitoring in one or more heart chamber.

Now turning to FIG. 3B, another system architecture for use in conjunction with embodiments of the invention is depicted. FIG. 3B is an exemplary system that may be utilized to deliver therapy by incorporating the system and method described above. Notably, the depicted system includes a sense amplifier 534 to sense electrical signals such as EGM signals using one or more leads placed within a respective chamber of the heart. These signals are used to determine atrial and ventricular depolarizations and Q-T length so that therapy delivery is provided in a safe manner. One or more physiological or hemodynamic signals may be sensed using sensors such as those discussed above. These additional signals, which are shown collectively provided on line 505, may be used to determine cardiac output so that therapy may be initiated, terminated, and/or optimized.

The system of FIG. 3B further includes a timer/controller to control the delivery of pacing pulses on output lines 500 and 502. This circuit, alone or in conjunction with microprocessor 524, controls interval lengths, pulse amplitudes, pulse lengths, and other waveform attributes associated with the pacing pulses. Output circuit 548 delivers high-voltage stimulation such as defibrillation shocks under the control of defibrillation control circuit 554.

Not all of the conventional interconnections of these voltages and signals are shown in either FIG. 3A or FIG. 3B and many other variations on the illustrated electronic circuitry are possible, as is known to those of skill in the art.

Figure 4:
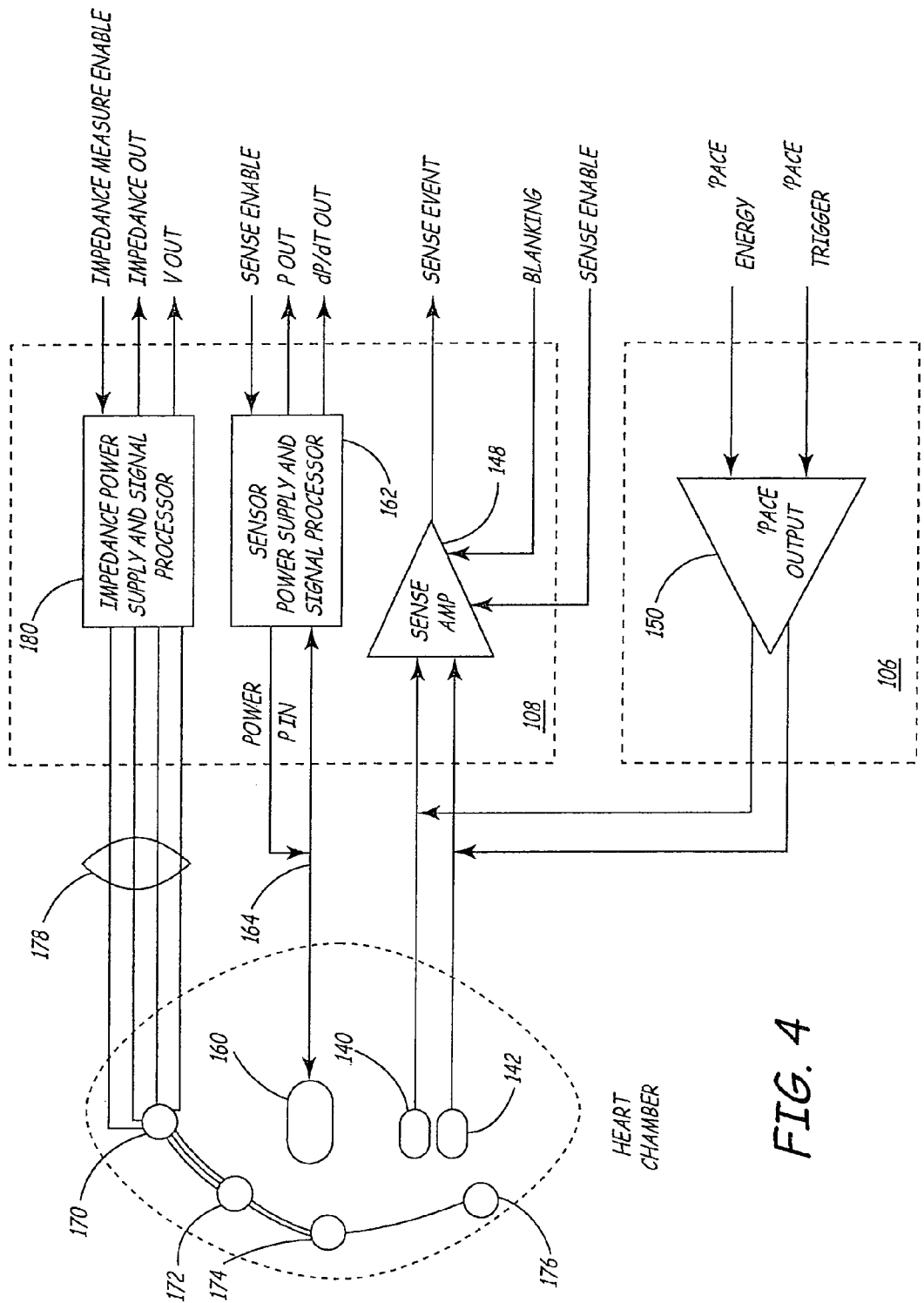
FIG. 4 is a simplified block diagram of a single monitoring and pacing channel for deriving pressure, impedance, and cardiac EGM signals employed in monitoring and optionally pacing the heart in accordance with embodiments of the invention.

FIG. 4 schematically illustrates one pacing, sensing, and parameter measuring channel in relation to one heart chamber. A pair of pace/sense electrodes 140,142, a sensor 160 (e.g., a pressure, saturated oxygen, flow, pH or the like), and a plurality, e.g., four, impedance-measuring electrodes 170, 172, 174, 176 are located in operative relation to the heart chamber. The pair of pace/sense electrodes 140, 142 are located in operative relation to the heart chamber and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled. The blanking signal is provided by control and timing system 102 upon delivery of a pacing pulse or pulse train to disconnect the sense amplifier inputs from the lead conductors 144 and 146 for a short blanking period in a manner well known in the art. When sense amplifier 148 is enabled and is not blanked, it senses the electrical signals of the heart, referred to as the EGM, in the heart chamber. The sense amplifier provides a sense event signal signifying the contraction of the heart chamber commencing a heart cycle based upon characteristics of the EGM, typically the P-wave when the heart chamber is the RA or LA and the R-wave, when the heart chamber is the RV or LV, in a manner well known in the pacing art.

The pair of pace/sense electrodes 140, 142 are also coupled through lead conductors 144 and 146, respectively, to the output of a pulse generator 150. The pulse generator 150, within pacing delivery system 106, selectively provides a pacing pulse to electrodes 140, 142 in response to a PACE trigger signal generated at the time-out of the EI timer within control and timing system 102 in a manner well known in the pacing art. Or, the pulse generator 150 selectively provides a pulse or pulse train to electrodes 140, 142 in response to a PACE trigger signal generated at the time-out of a timer within control and timing system 102.

The sensor 160 and/or other physiologic sensor is coupled to a sensor power supply and signal processor 162 within the input signal processing circuit 108 through a set of lead conductors 164 that convey power to the sensor 160 and sampled blood pressure P signals from the sensor 160 to the sensor power supply and signal processor 162. The sensor power supply and signal processor 162 samples the blood pressure impinging upon a transducer surface of the sensor 160 located within the heart chamber when enabled by a sense enable signal from the control and timing system 102. As an example, absolute pressure P, developed pressure DP and pressure rate of change dP/dt sample values can be developed by sensor power supply and signal processor unit 162 or by the control and timing system 102 for storage and processing as described further below. The sensor 160 and a sensor power supply and signal processor 162 may take the form disclosed in commonly assigned U.S. Pat. No. 5,564,434.

The set of impedance electrodes 170, 172, 174 and 176 is coupled by a set of conductors 178 and is formed as a lead that is coupled to the impedance power supply and signal processor 180. Impedance-based measurements of cardiac parameters such as stroke volume are known in the art such as having an impedance lead having plural pairs of spaced surface electrodes located within the heart chamber. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

A measure of heart chamber volume V is provided by the set of impedance electrodes 170, 172, 174 and 176 when the impedance power supply and signal processor 180 is enabled by an impedance measure enable signal provided by control and timing system 102. A fixed current carrier signal is applied between the pairs of impedance electrodes and the voltage of the signal is modulated by the impedance through the blood and heart muscle which varies as distance between the impedance electrodes varies. Thus, the calculation of the heart chamber volume V signals from impedance measurements between selected pairs of impedance electrodes 170, 172, 174 and 176 occurs during the contraction and relaxation of the heart chamber that moves the spaced apart electrode pairs closer together and farther apart, respectively, due to the heart wall movement or the tidal flow of blood out of and then into the heart chamber. Raw signals are demodulated, digitized, and processed to obtain an extrapolated impedance value. When this value is divided into the product of blood resistivity times the square of the distance between the pairs of spaced electrodes, the result is a measure of instantaneous heart chamber volume V within the heart chamber.

The present embodiment relates to the measurement of physiological parameters in the coronary sinus (CS) to measure, monitor, and optimize left ventricular performance. The blood of the coronaries is drained via the coronary veins through the coronary sinus into the right atrium. The blood passing through the CS, thus reflects the physiological state of the left ventricular myocardium. Different physiological parameters that can either acutely or chronically be monitored in the CS are proposed to be used to monitor or optimize the left ventricular performance. Any physiological parameter can be monitored without departing from the spirit of the invention, however, for purposes of the detailed description reference will be made to CS blood pressure, CS blood flow velocity, CS oxygen saturation, CS glucose concentration, and CS blood temperature.

The coronary blood flow is governed by the arterio-venous pressure difference and coronary vascular hemodynamic impedance. The arterial pressure as well as the coronary vascular impedance (CVI) (hemodynamic impedance) is modulated during the cardiac cycle. The CVI is minimal during the diastole and maximal during the systole. In addition, the CVI is directly related o the left ventricular pressure (more precisely the trans-mural left ventricular pressure). During systole the coronaries as well as the sub-endocardial smaller vessels and capillaries tend to be more compressed than during diastole, when the ventricular pressure is low, thus resulting in an increased CVI. The total length of diastole vs. the systole further determines CS blood flow.

Total coronary flow is dependent on several factors including: arterio-venous coronary pressure difference, coronary vascular impedance, which depends on the cardiac cycle and the ventricular filling pressure, and the duration of the diastole. Major coronary flow occurs during the diastole and is impaired by raised diastolic intra-ventricular pressures and short diastoles (or long systoles). One embodiment of the present invention suggests measuring the diastolic flow and/or diastolic/systolic flow ratio. Diastolic flow will be determined as the (maximal) flow during cardiac diastole. Diastole and Systole can be based on the ECG or EGM. Systolic flow can be determined similarly as the (minimal) flow during cardiac systole. These measurements can then be used as performance indicators of the left ventricle, as a measure of cardiac dyssynchrony, to automatically monitor and identify myocardial ischemia, used as a measure of hemodynamics, and optimize coronary perfusion using a drug pump therapy, pacing, and/or bi-ventricular pacing.

Figure 5:
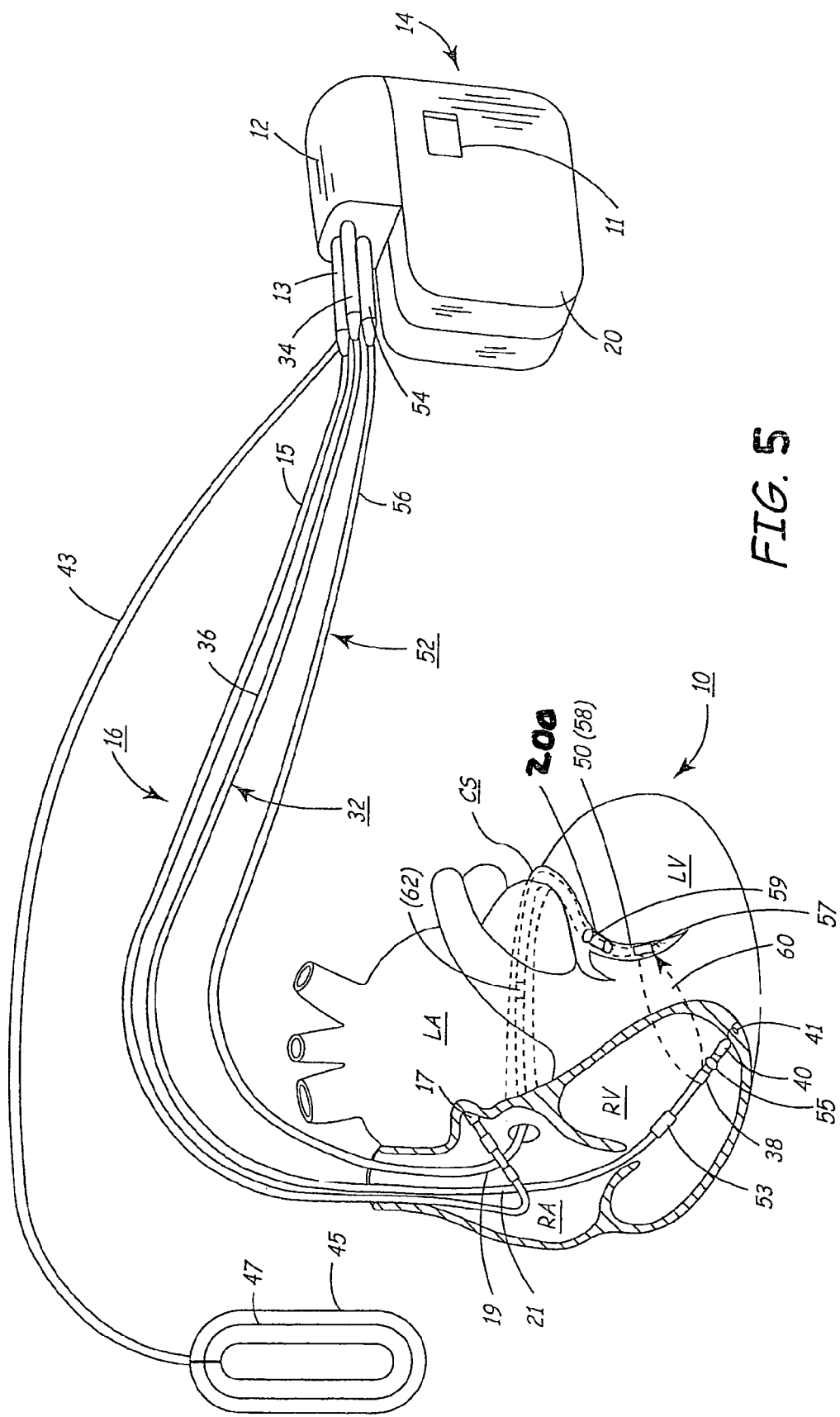
FIG. 5 is a schematic diagram depicting a multi-channel, atrial and bi-ventricular, monitoring/pacing IMD having a coronary sinus sensor in an embodiment of the present invention.

With reference to FIG. 5, a schematic diagram depicting a multi-channel, atrial and bi-ventricular, monitoring/pacing IMD having a coronary sinus sensor in an embodiment of the present invention is shown. Sensor 200 is mounted on lead 52 for measurement of the blood flow velocity within the heart as described above. IMD 14 is shown as including blood flow sensor 200, which is an electrochemical or ultrasonic intravascular Doppler mounted on lead 52, such as those disclosed in U.S. Pat. No. 6,754,532 herein incorporated by reference in their entirety. However, sensor 200 can be most any type of blood flow sensor such as a light scattering sensor or by indirectly measuring flow derived from pressure and/or pressure changes in the CS. Blood flow sensor 200 typically (although not necessarily) provides a flow rate signal representing the velocity of blood flowing through the heart. Blood flow sensor 200 is connected to a flow signal acquisition circuit located inside IMD 14. The output signal provided by flow sensor 200 is coupled to input/output circuit 108. Input/output circuit 108 contains analog circuits for interfacing to heart 10, blood flow sensor 200, and circuits for the application of stimulating pulses to heart 10. Left ventricular pacing lead 52 is inserted such that a blood flow sensor 200 within pacing electrode 52 produces a signal representing the flow rate of blood through the coronary sinus. As described in detail below, microprocessor 102 and pacing circuitry control the pacing intervals as a function of the blood flow rate signal received from flow sensor 200 of left ventricular pacing lead 52.

There are several ways IMD 14 will know when the left ventricular contraction has been optimized and when therapy is needed. It is well know that there are various aspects, that will affect ventricular contraction, especially maximal pacing rate, AV-delay and VV-delay. Each of these could be controlled independently using a different Variable analyzed e.g., measuring CS $dp/dt_{max}$ over a period of time (e.g. 5 minutes or several hours). This will provide an optimal heart rate where $dp/dt_{max}$ will fluctuate for higher and lower heart rates. This will allow the setting of an upper tracking rate and upper pacing rate. In another embodiment, VV-timing can be optimized by simultaneously maximizing the left ventricular diastolic filling and minimize the left ventricular ejection time. This can be achieved to evaluating the left ventricular diastolic filling and ejection times from a CS pressure or flow curve. The ratio of the CS Diastolic length/CS Systolic times normalized for the RR interval could also be used. In another embodiment, the AV timing could be optimized by maximizing the total left ventricular filling time (diastolic length) and/or the left ventricular end diastolic pressure. Both of these can be assessed using the CS flow or pressure signals.

In an alternative embodiment, sensor 200 could be a pressure sensor 200, such as is described in U.S. Pat. No. 5,129,394 herein incorporated by reference in its entirety, located within the coronary vein adjacent to the left ventricle. Pressure can be measured with fiber optic techniques, piezo resistive, and capacitive techniques without departing from the spirit of the invention. Pressure parameters can also be derived in relation to another sensed signal, for example the ECG. E.g., The value of the pressure at a specific time dt after the R peak, or a specific fraction of the RR interval after the R peak. In this position, pressure proportional to the systolic and diastolic pressure of the left ventricle may be sensed. The signals derived from pressure sensor 200 and applied to the microprocessor/memory 102 may be employed to develop pulse, systolic and diastolic pressure values, long term mean or average values of these pressure values or both, short term mean or average values of the same pressures, the time derivatives (dP/dt) of the pressure signals and corresponding mean or average values thereof over short and long terms and the gross rate of change ($\Delta P/\Delta t$). The microprocessor/memory 102 may include specific circuits for differentiating the pressure signal, measuring the peak pulse, systolic and diastolic pressures and the mean and gross rate of change of these values. For example, the calculation of the mean blood pressure may be carried out in various manners. For instance, the microprocessor/memory 102 may consist of a mean value rectifying circuit having a suitable time constant including two peak detecting amplifiers which are connected to the signal from the pressure transducer with opposite polarities so that the one amplifier produces an output signal representing the systolic blood pressure, whereas the other amplifier produces an output signal representing the diastolic blood pressure. A high diastolic pressure could indicate a high LV diastolic pressure, which is the target function for AV-optimization. Thus for AV-optimization, AV timing and VV timing could be slightly changed to see if this leads to a better CS measure and thus LV hemodynamic.

Figure 5A:
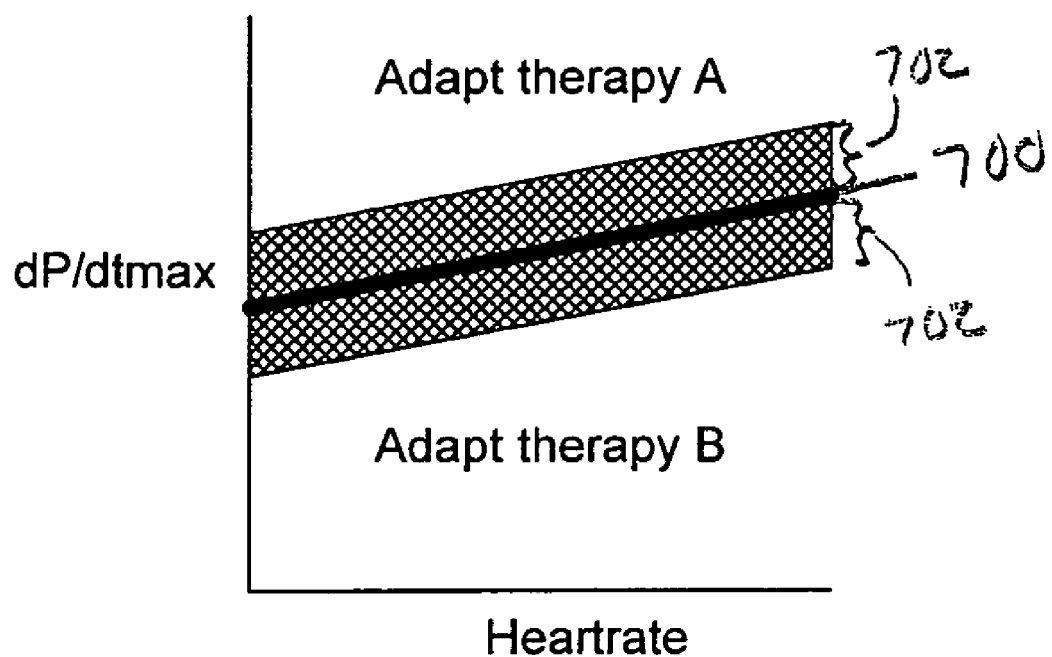
FIG. 5A is a graph showing the optimization of pacing therapy based upon blood pressure in the coronary sinus as a function of pressure versus heart rate in an embodiment of the present invention.

With reference to FIG. 5A, a graph showing the optimization of pacing therapy based upon blood pressure in the coronary sinus as a function of pressure versus heart rate in an embodiment of the present invention is shown. There exists an optimal $dP/dt_{max}$ designated by black line 700. The optimum pacing therapy depends on the heart rate of the patient. A certain bandwidth 702 around the optimum value is acceptable, but when the measured $dp/dt_{max}$ is outside bandwidth 702 the therapy is adapted as discussed below. This therapy can be different based upon whether the measured value is in region A or B. At the time of implant the $dp/dt_{max}$ is maximized at a fixed heart rate using a priority list strategy or other techniques known in the art. From this point the position of the curve along the y-axis is known. The bandwidth can be predetermined or set by the implanting clinician based upon the patient's health. If the $dp/dt_{max}$ gets into region B the pacing therapy would be adapted according to the same priority list as referred to above, in order to get the value back in the band. If it gets into region A, the condition of the heart has improved due to the therapy, and the whole curve is shifted upwards so the value is just inside the band. That is, in region A, therapy does not need to be adapted.

The positioning of the sensor is helpful to the present invention. A good sensor position could be determined at the time of implant based upon a display of the sensor signal on a IMD programmer utilizing selection criteria such as a pressure reading of 10 mmHg. Typically the sensor is advanced in the CS while monitoring the pressure signal on a display. When it is still relatively close to the RA the pressure signal looks just like the RA pressure, with an A and V peak and low amplitude, around 5 mmHg. When the sensor is advanced to more distal positions, the pressure signal will gradually change shape towards a more ventricular like pattern of higher amplitude around 10 mmHg. When the sensor is advanced even more distally, very large pressures approaching an LV pressure of 100 mmHg might be observed. If the extreme proximal and distal situations are prevented, the signal is usable. In this procedure it is helpful to have a venogram to have a visual representation of the veins and position of the sensor in it. Now this may create some difficulties due to the fixed distance between electrode 50 and sensor 200. Therefore, it is contemplated that lead 52 could have multiple electrodes at the distal end, which could be selected. In this way the sensor could be placed at an optimum position and then an optimum pacing position can be selected by choosing from various electrodes.

In another embodiment of the present invention, sensor 200 can be an oxygen sensor, such as disclosed in U.S. Pat. No. 5,213,098 herein incorporated by reference in its entirety. Oxygen can be measured with fiber optic or electrochemical techniques without departing from the spirit of the invention. Oxygen sensor 200 could detect oxygen extraction in the CS, which similar to the above discussion regarding blood pressure and flow, can be an indicator of myocardial perfusion. Decreased perfusion, e.g., due to cardiac dyssynchrony and elevated left ventricular pressure will lead to increased extraction of oxygen from the blood. In addition for the case of successful resynchronization of the left ventricle, the left ventricular efficiency increases as the same cardiac work is performed at a reduced amount of oxygen cost, leading to a lower oxygen extraction. Oxygen sensor 200 is connected to a signal acquisition circuit located inside IMD 14. The output signal provided by oxygen sensor 200 is coupled to input/ output circuit 108. Input/output circuit 108 contains analog circuits for interfacing to heart 10, oxygen sensor 200, and circuits for the application of stimulating pulses to heart 10. Left ventricular pacing lead 52 is inserted such that oxygen sensor 200 within pacing electrode 52 produces a signal representing the oxygen content in the blood through the coronary sinus. As described in detail below, microprocessor 102 and pacing circuitry control the pacing intervals as a function of the oxygen signal received from oxygen sensor 200 of left ventricular pacing lead 52. Uncoordinated contraction of the left ventricle in patients with cardiac dyssynchrony is very inefficient. Resynchronization and adjustments of resynchronization by VV-timing directly affect the ventricular efficiency and will affect the oxygen extraction, thus the amount of oxygen that is consumed by the myocardium.

In another embodiment of the present invention, sensor 200 can be a glucose sensor. Glucose sensor can be any glucose sensor, such as disclosed in U.S. Pat. No. 6,666,821 herein incorporated by reference in its entirety. Glucose sensors usually operate enzymatically. Glucose is oxidized using a matrix bound enzyme in the presence of oxygen from the blood. A standard electrochemical oxygen sensor can be used that detects the amount of oxygen, which is inversely proportional to the amount of glucose in the blood. Glucose is metabolized in the myocardium. The level and utilization and extraction of glucose is directly related to the left ventricular performance, similar to the above discussion on blood flow and CS oxygen saturation. Glucose sensor 200 is connected to a signal acquisition circuit located inside IMD 14. The output signal provided by glucose sensor 200 is coupled to input/output circuit 108. Input/output circuit 108 contains analog circuits for interfacing to heart 10, glucose 200, and circuits for the application of stimulating pulses to heart 10. Left ventricular pacing lead 52 is inserted such that glucose sensor 200 within pacing electrode 52 produces a signal representing the glucose content of blood through the coronary sinus. As described in detail below, microprocessor 102 and pacing circuitry control the pacing intervals as a function of the glucose content signal received from glucose sensor 200 of left ventricular pacing lead 52. Glucose could be a useful monitoring variable. Under extreme work load and in the situation of heart failure, it is know that the heart is switching from fatty acid burning to glucose utilization. Discordant contraction causing dyssynchrony will thus have high glucose extraction. If there is optimal resynchronization the myocardial contraction becomes more coordinate and more efficient again thus having a lower glucose extraction.

In another embodiment of the present invention, sensor 200 can be a lactate or CS proton sensor. Lactate could be further oxidized similar to glucose and the same techniques could be applied as discussed above for glucose. PH can be directly measured using ChemFETs or other electrochemical sensors. It is the presence of lactate that leads to a decrease in pH. Lactate and CS proton concentration provide an estimate of the degree of oxidative metabolism. The myocardium usually operates aerobically. Myocardial overload and reduced perfusion can cause a switch to un-aerobic metabolism. Thus lactate/pH can be used to monitor and optimize perfusion and cardiac workload. Lactate/proton sensor 200 is connected to a signal acquisition circuit located inside IMD 14. The output signal provided by lactate/proton sensor 200 is coupled to input/output circuit 108. Input/output circuit 108 contains analog circuits for interfacing to heart 10, lactate/proton sensor 200, and circuits for the application of stimulating pulses to heart 10. Left ventricular pacing lead 52 is inserted such that a lactate/proton sensor 200 within pacing electrode 52 produces a signal representing the level of lactate or protons in the blood through the coronary sinus. As described in detail below, microprocessor 102 and pacing circuitry control the pacing intervals as a function of the lactate/proton signal received from lactate/proton sensor 200 of left ventricular pacing lead 52. Similar to the discussion for oxygen and glucose above, minimizing lactate would be the target function for optimal programming setting.

Figure 5B:
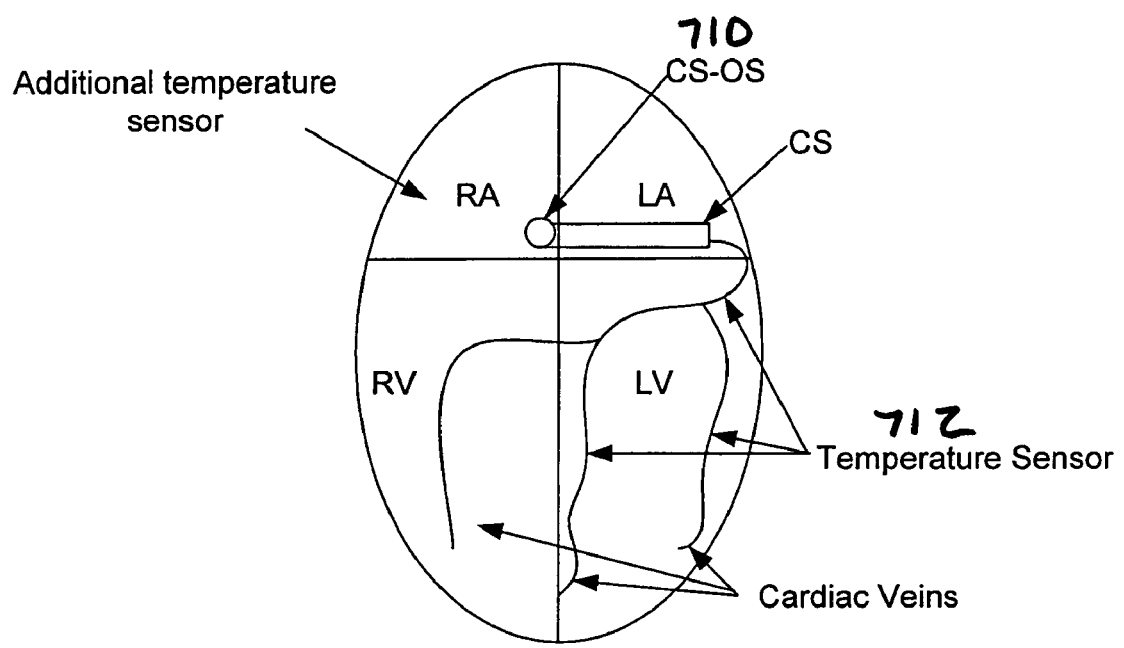
FIG. 5B is a diagram showing multiple temperature sensors used to optimize the heart hemodynamics in an embodiment of the present invention.

In another embodiment of the present invention, sensor 200 can be a blood temperature sensor. Temperature sensor can be any temperature sensor, such as disclosed in U.S. Pat. No. 5,336,244 herein incorporated by reference in its entirety. A temperature difference sensor would be especially helpful in that it would nullify the influence of changes in the overall body temperature. What is meant is that there are two locations at which the temperature is measured, one sensor 710 (FIG. 5B) in the RA, the other 712 (FIG. 5B) located somewhere in the CS or further in the cardiac veins. The difference between these two is a measure for how much warmer the blood coming from the heart itself is then the blood coming from the rest of the body. This is a measure for the efficiency with which the heart performs work. If only the CS temperature was measured, and it would for example be rising, it would be more difficult to discriminate between a total rise in patient temperature and a rise in CS blood temperature related to worse efficiency of the heart.

Temperature can be measured with a thermocouple or thermistor without departing from the spirit of the invention. Blood temperature is easy to measure and provides an estimate of the myocardial perfusion and workload. Temperature sensor 200 is connected to a signal acquisition circuit located inside IMD 14. The output signal provided by temperature sensor 200 is coupled to input/output circuit 108. Input/output circuit 108 contains analog circuits for interfacing to heart 10, temperature sensor 200, and circuits for the application of stimulating pulses to heart 10. Left ventricular pacing lead 52 is inserted such that temperature sensor 200 within pacing electrode 52 produces a signal representing the temperature of blood through the coronary sinus. As described in detail below, microprocessor 102 and pacing circuitry control the pacing intervals as a function of the temperature signal received from temperature sensor 200 of left ventricular pacing lead 52. An algorithm would seek to reduce CS blood temperature to a normal blood temperature (98.6° F.) to be optimize the pacing. Similar to the discussions above blood temperature provides information on the myocardial work performed. In general increasing myocardial-working efficiency is beneficial and will affect temperature. The more efficient the heart performs works the less heat is produced so the temperature difference should be minimized. The optimum temperature difference is determined at the time of implant and is around 0.1 Celcius. If the temperature increases above this value plus a certain band taking into account the physical activity as stated next, the therapy should be adapted. If the temperature difference drops the whole curve can be shifted down, the condition of the heart has improved due to therapy. The changing mechanisms of burning when the myocardium is overloaded will also be visible in the temperature difference. The lower the difference in temperature the better. The physical activity of the individual should be considered in all of these cases in order to differentiate increasing myocardial workload due to more exercise or increasing myocardial workload due to worsened myocardial efficiency (e.g. dyssynchrony). This could be obtained from heart rate or accelerometers that measure the physical activity of the individual.

It is fully contemplated that each of these sensors could be utilized separately or together to monitor and optimize the pacing therapy for a patient. Further it is contemplated that multiple sensors of the same type can be used without departing from the spirit of the invention. An optimization algorithm, discussed below, can then process the incoming parameters and attempt to optimize cardio resynchronization therapy (CRT). The algorithm can operate with all, some, or one of the measured heart parameters in the optimization process. However, the more parameters measured and utilized the better. Thus, if the algorithm determines that not just one, but several measured parameters are indicating that the pacing therapy needs modification then the algorithm will indicate that pacing modification is needed and begin the optimization process. Likewise, if a majority of the measure parameters are indicating a pacing modification is needed, then the algorithm will indicate that pacing modification is needed. And, if a majority of the measure parameters are indicating that the heart is running optimally then the algorithm does nothing.

As discussed above the measured parameters can be used to monitor and/or optimize the left ventricular performance. As part of a monitoring function, the measured parameters could be stored in memory on IMD 14, thus creating an index of cardiac performance (left ventricular performance) and cardiac dysynchrony. This index can then be utilized by an implanting physician to determine optimized settings for IMD 14 to provide optimized pacing therapy. Additionally, the algorithms discussed below can be used to automatically program the settings of IMD 14 based upon optimizing the measured parameters within the index. In chronic use, the measured parameters can be used to optimize the pacing therapy throughout the life of the patient. As a patient ages the status of the heart changes. Typically as a heart ages it performs less optimally. Therefore, the algorithm can monitor the index of measured parameters over the life of the patient and optimize the pacing therapy to account for any natural changes in the hearts operation.

With reference to FIGS. 6A-C, a diagram of lead delivery catheter in an embodiment of the present invention is shown. In acute use, IMD 14 could further have a lead delivery tool such as is shown in FIGS. 7A-C, with sensors coupled thereto. In FIG. 6A, catheter 400 has a lead delivery port 402 where leads 16, 32, and 52 can be routed through to be implanted within the heart. Additionally catheter 400 can have a blood sampling port 404. When desired, the physician can sample blood through port 404 and tube 406. The physician can then test the blood for various quantities, such as oxygen and metal ions using methods known in the art. Based upon these values the physician can make a determination as to the desired pacing therapy. The physician can also input the blood values into an external programmer where the algorithm would automatically determine, from the indexes, a pacing therapy.

In FIG. 6B, catheter 408 has a lead delivery port 410 where leads 16, 32, and 52 can be routed through to be implanted within the heart. Catheter 408 can also have biochemical sensors 412 for detecting BNP and/or lactate using methods known in the art. The biochemical values are then sent up line 414 to an external programmer containing the algorithm discussed below which would begin the optimization process. The algorithm can be within implantable device 14 or located on an external programmer.

In FIG. 6C, catheter 416 has a lead delivery port 418 where leads 16, 32, and 52 can be routed through to be implanted within the heart. Catheter 416 can also have pressure sensors 420 for detecting left and/or right ventricular pressure using methods known in the art. The pressure readings are sent up line 422 to an external programmer containing the algorithm discussed above which runs the optimization process. VV-timing optimization aims at minimizing the left ventricular filling pressure (while keeping all other settings constant). A lowering of the left ventricular filling pressure (diastolic pressure), will lead to an increased CS pressure. AV-timing optimization aims at maximizing the left ventricular filling pressure (while keeping all other settings constant). An increase in left ventricular filling pressure can be monitored by a decrease in CS pressure. Optimal AV- and VV-timing will, in addition, directly positively affect dp/dp(max) (a measure of cardiac contractility). As such AV- and VV-timing can be optimized by optimizing left ventricular dp/dt(max). Left ventricular dp/dt(max) can be measured by CS dp/dt(max) and be used for optimization of AV- and VV-timing.

Currently IMD implantation is optimized by making echo images of the heart with an external transducer. The echo images assist the clinician in finding preferred areas of the heart in which to place the leads. For example, detecting areas of ischema, fatty tissue, or dead cells, which do not electrically conduct very well. While somewhat effective, this method is not totally accurate, not very reproducible, and it is operator dependent. Even if good information is obtained from the echo images, the manual setting of the pacemaker is a time consuming process. It will help the clinician if they can have a choice to program some of the IMD setting automatically. This will decrease the chance of error and increase the standardization of the therapy over large patient groups and between physicians. Programming is usually based on the experience of a physician in obtaining relevant physiological parameters. Assessment of asynchrony is based on multiple different approaches, which are difficult to compare. Upper tracking rate/upper pacing rate settings are usually not done at all based on empirical assessment. The system could be utilized in many fashions including: a cardiac performance monitor where the measured parameters would be stored in the index and evaluated to determine cardiac operation; an angina monitor; used for automatic programming of a pacemaker system during implantation; and atrio-ventricular/ventricular-ventricular optimization by monitoring the measured parameters and then optimizing the pacing therapy.

Figure 7:
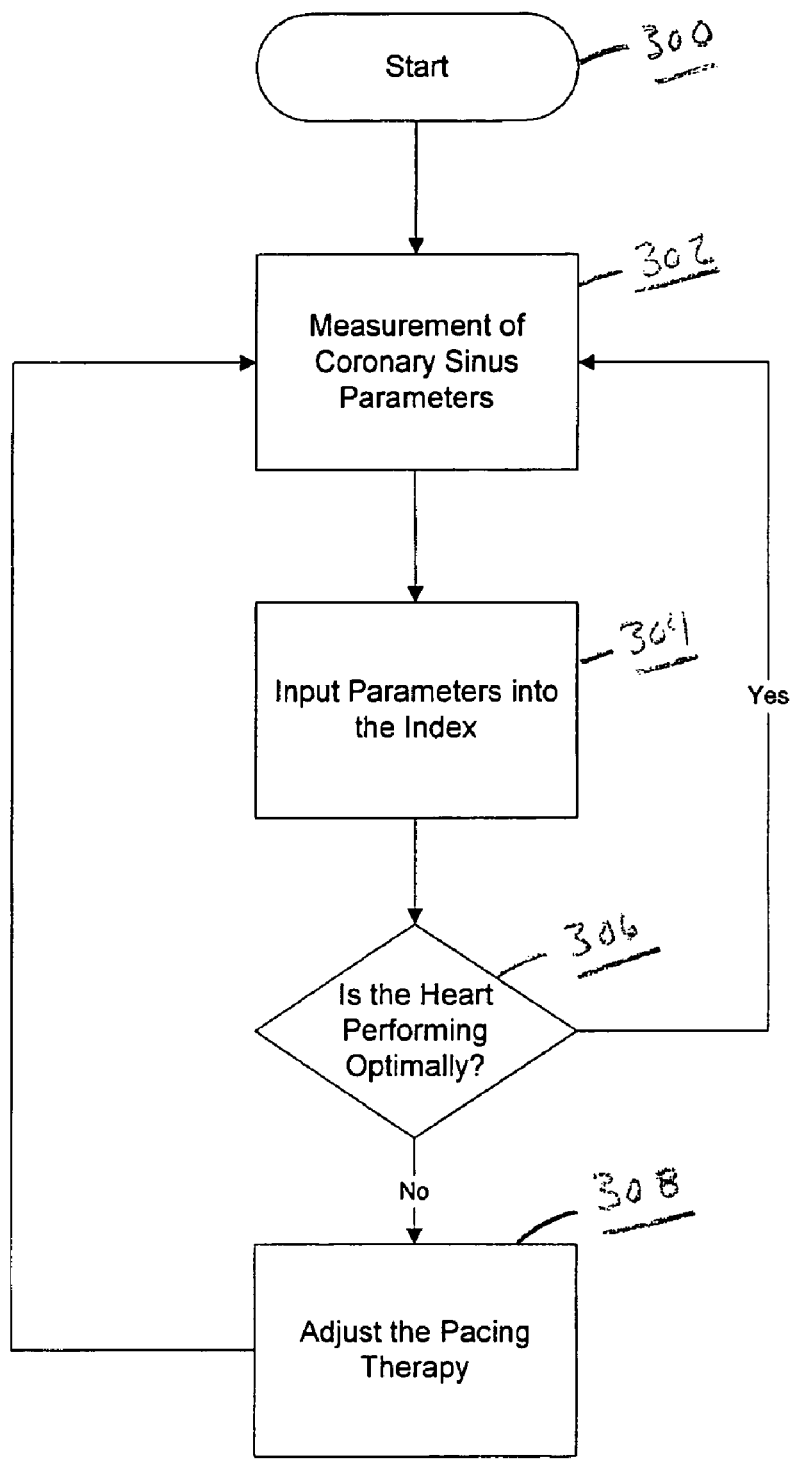
FIG. 7 is an upper level flow diagram of an algorithm for pacing optimization in an embodiment of the present invention.

With reference to FIG. 7, an upper level flow diagram of an algorithm for pacing optimization in an embodiment of the present invention is shown. State 300 would typically represent IMD 14 being powered up upon implementation, however, this could also represent any other powering up state, such as a restart, or the beginning of a reprogramming process. IMD 14 would then immediately begin to collect measurements from whatever coronary sinus sensors where being used such as those discussed above. IMD would also be collecting commonly collected heart data such as EGM at state 302. This data is then inputted into the index memory where it is collected for evaluation at state 304. At state 306, the data is evaluated to determine if the heart is functioning properly. Each of the parameters is evaluated to determine if they are within certain parameters. These parameters are preset and represent a typical properly functioning heart. For example, oxygen extraction by the myocardium under a specific exercise situation should not exceed a preset limit. For example, the oxygen saturation at mean physical exercise and at heart rates of approximately 120 bpm should not be lower than 80%. If it goes below 80% than a pacing adjustment is performed. It is understood that all the parameters could be evaluated or just one depending on the patient and the physician's preference. If the heart is functioning properly, the algorithm returns to state 302 and the process begins again. If the heart is not functioning properly, the algorithm proceeds to state 308 where the pacing therapy is adjusted to optimize heart performance. Typical changes to pacing therapy will be upper tracking rate/pacing rate, AV-delay, and VV-delay. Each of these will affect the cardiac function in a different way, and would need to be assessed slightly differently. Upon adjustment of the pacing therapy, the algorithm would return to state 302 and begin the process all over again.

Figure 8:
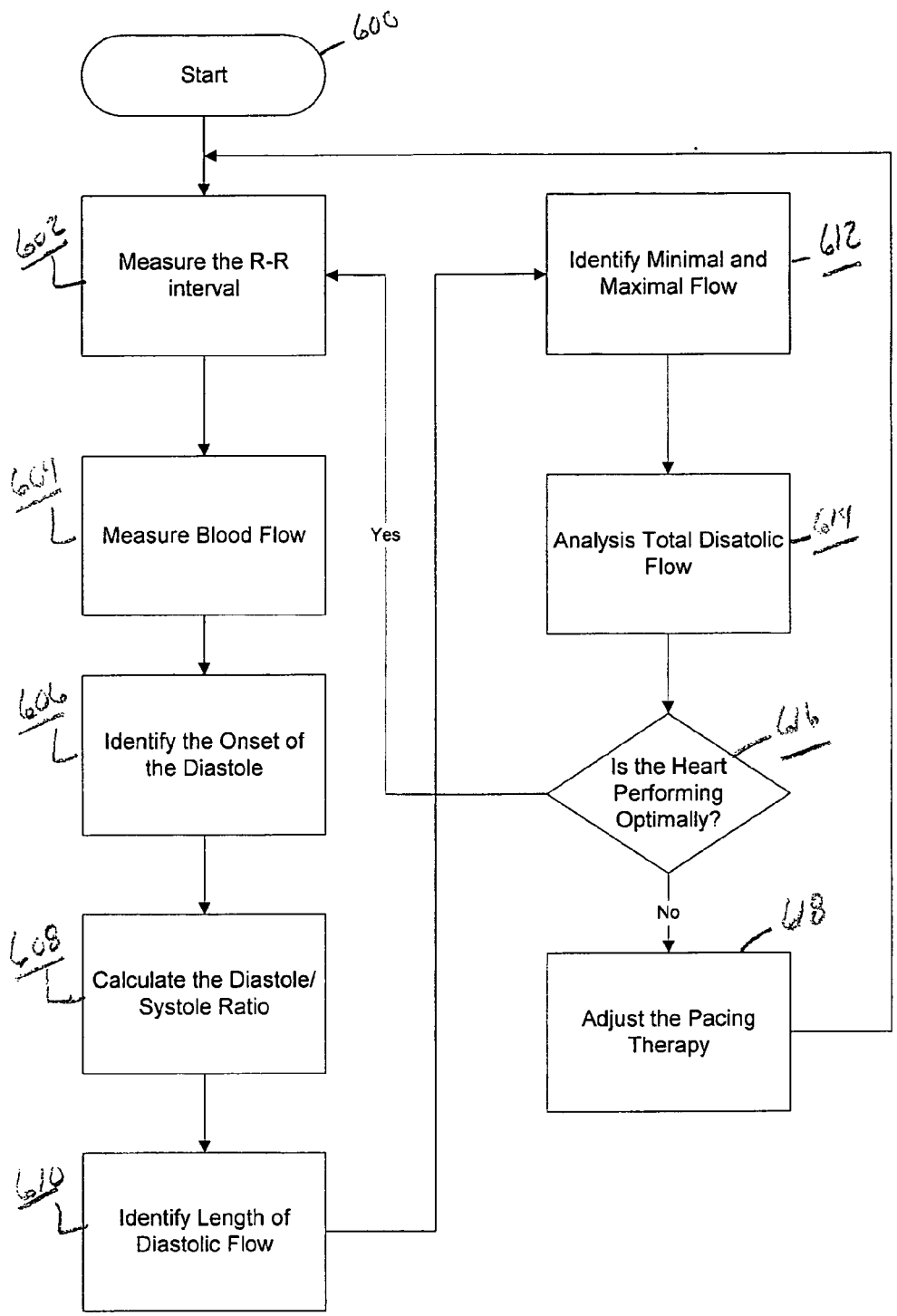
FIG. 8 is a flow diagram of an algorithm for pacing optimization in an embodiment of the present invention.

With reference to FIG. 8, a flow diagram of an algorithm for pacing optimization in an embodiment of the present invention is shown. Similar to above, state 600 would represent an initial power up of IMD 14, a power or processor reset, or a reprogramming of IMD 14. Upon state 600, IMD would begin to measure the R-R interval from the QRST waveform at state 602. This measurement represents diastolic and systolic length needed to be normalized to the current RR-interval. At state 604, IMD 14 would measure the blood flow through pressure measurement or using a direct flow method. The blood flow will increase at onset of diastole and decrease oat the end of diastole, so that the blood flow will be used to measure, when diastole and systole occur and what is the diastolic and/or systolic length. Through these measurements IMD 14 is able to identify the onset of diastole as a function of the onset of coronary flow after ventricular activation at state 606. IMD 14 then calculates the diastole/systole ratio as a possible indicator of heart dysynchrony at state 608. IMD 14 also identifies the length of diastolic flow (state 610), minimal and maximal flow (state 612), and flow onset pattern (state 614) all of which are indicators of heart dysynchrony. IMD 14 then analyses all of these parameters to may a determination of whether the heart is operating optimally or whether the current pacing therapy needs to be modified to better optimize performance of the heart at state 616. At state 618, IMD inquires as to whether the heart is performing optimally. If the heart is operating optimally, IMD 14 returns to state 602 to begin the process again. If the heart is not operating optimally, IMD 14 proceeds to state 620 where the pacing therapy is adjusted based upon the measured parameters. Since the different measured parameters may interact with each other, a sequential optimization can be envisioned. In such a scenario a priority list would give the sequence of parameters to be optimized and adjusted after each other. E.g. VV-first, AV-second, heart rate third. Therefore, VV-timing is adjusted iteratively until an optimal function is obtained while all other variables remained constant. Then the AV timing is adjusted until optimal function is obtained and so forth. After the pacing therapy is adjusted, IMD 14 returns to state 602 to begin the process all over again. This algorithm is repeated iteratively to constantly monitor the heart for optimum performance.

Figure 9B:
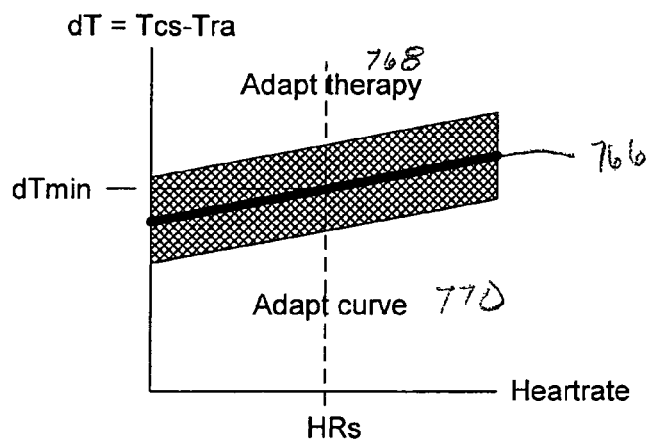
FIG. 9B is a graph showing the optimization of pacing therapy based upon blood temperature in the coronary sinus in an embodiment of the present invention.
Figure 9A:
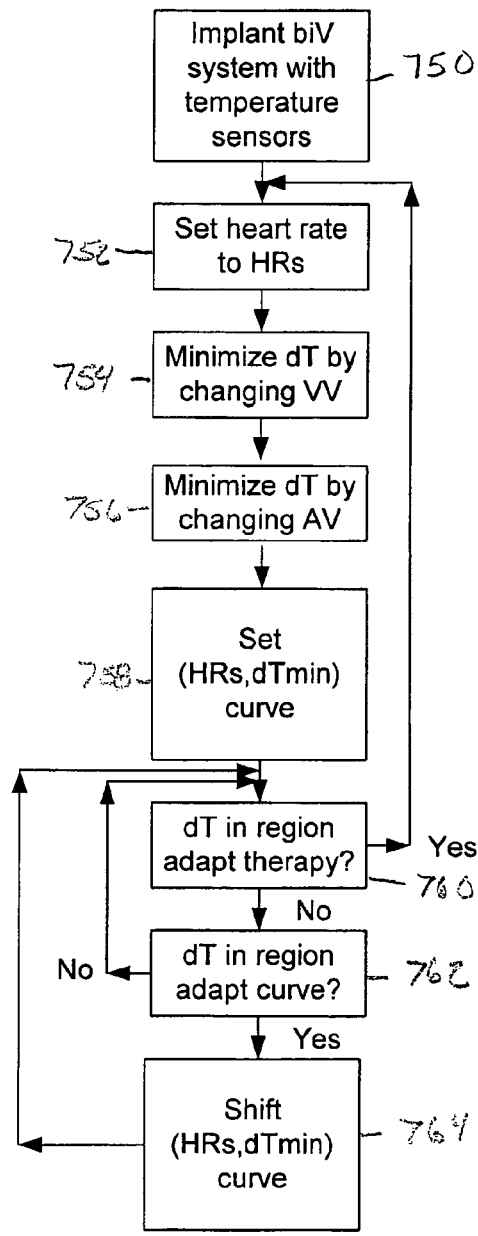
FIG. 9A is a flow diagram of an algorithm for pacing optimization based upon blood temperature in an embodiment of the present invention.

With reference to FIG. 9A, a flow diagram of an algorithm for pacing optimization in an embodiment of the present invention is shown. Initially at state 750 the bi-ventricular pacing IMD 14 having multiple temperature sensors is implanted. As discussed above, typically one sensor is implanted in the RA and the other in the CS. The implanting clinician can then program the desired heart rate for the patient at state 752. At state 754 IMD 14 can begin hemodynamic optimization by modifying the ventricle to ventricle (VV) pacing timing. Also at state 756 IMD 14 can begin to minimize the difference in temperature by modifying the pacing timing between the atrium and ventricles (AV). It is of note that states 754 and 756 do not have to be performed in the order shown in FIG. 9A. Further, it is noted that states 754 and 756 do not both have to be performed during the optimization process. In the optimization process, either state 754 or 756 can be performed without departing from the spirit of the invention. When a minimum difference in temperature is reached using the modification of VV and AV pacing therapies, differential temperature optimization curve 766 (FIG. 9B) is set and stored in memory at state 758. Differential temperature is defined as the difference in the blood temperature in the coronary sinus and the right atrium. IMD 14 continuously monitors the differential temperature. At state 760 IMD 14 determines whether the difference in temperature is in region 768 above curve 766. If the difference in temperature is within region 768, IMD 14 returns to state 752 to begin the optimization process again by setting a new heart rate and modifying the VV and AV timing. If the difference in temperature is not within region 768, IMD 14 then determines if the difference in temperature is within region 770 at state 762. If the difference in temperature is not within region 770, IMD 14 then returns to state 760 to determine if the difference in temperature is within region 768. If the difference in temperature is within region 770, IMD 14 then shifts optimization curve 766 to reflect the improved operation of the heart. Thus as the heart's hemodynamics improves, IMD will continue to set new optimization curves to base the optimization therapy upon. The algorithm of FIG. 9A can also be used to optimize heart performance based on lactate, PH, proton, and glucose extraction levels in the CS as it is desirable to minimize each variable.

Figure 10:
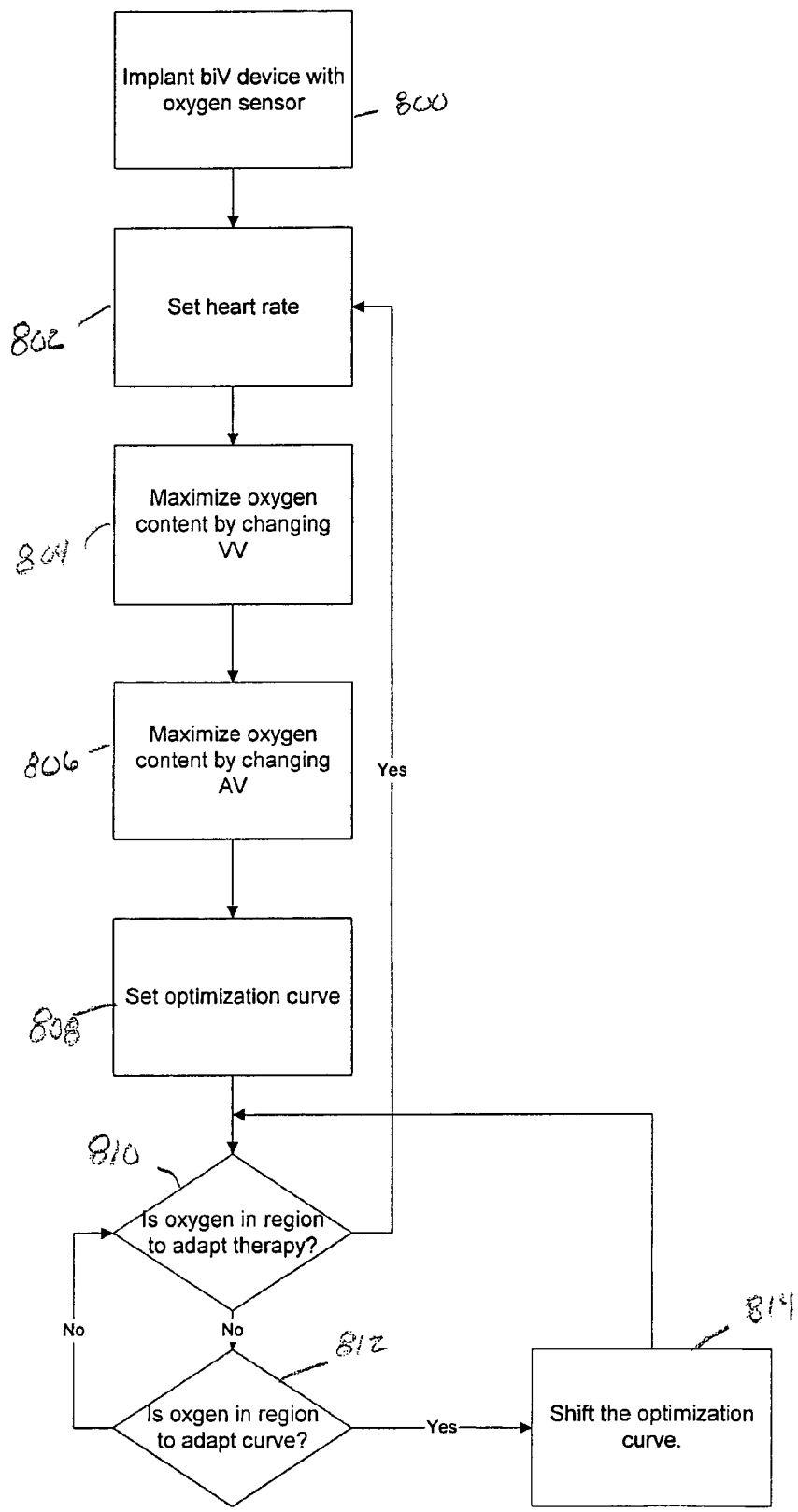
FIG. 10 is a flow diagram of an algorithm for pacing optimization based upon blood oxygen levels in an embodiment of the present invention.

With reference to FIG. 10, a flow diagram of an algorithm for pacing optimization in an embodiment of the present invention is shown. Initially at state 800 IMD 14 having an oxygen sensor is implanted. The implanting clinician can then program an initial desired heart rate for the patient at state 802. At state 804 IMD 14 can begin hemodynamic optimization by modifying the ventricle to ventricle (VV) pacing timing. Also at state 806 IMD 14 can begin to maximize the oxygen content in the coronary sinus by modifying the pacing timing between the atrium and ventricles (AV). It is of note that states 804 and 806 do not have to be performed in the order shown in FIG. 10. Further, it is noted that states 804 and 806 do not both have to be performed during the optimization process. In the optimization process, either state 804 or 806 can be performed without departing from the spirit of the invention. When a maximum oxygen level is reached using the modification of VV and AV pacing therapies, an oxygen curve (similar to the temperature curve) is set and stored in memory at state 808. IMD 14 continuously monitors the oxygen level in the coronary sinus. At state 810 IMD 14 determines whether the oxygen level is in a region below the oxygen curve. If the oxygen level is below the curve, IMD 14 returns to state 802 to begin the optimization process again by setting a new heart rate and modifying the VV and AV timing. If the oxygen level is not below the curve, IMD 14 then determines if the oxygen level is above the curve at state 812. If the oxygen level is not above the oxygen curve, IMD 14 then returns to state 760 to determine if the oxygen level is below the curve. If the oxygen level is above the curve, IMD 14 then shifts the optimization curve to reflect the improved operation of the heart. Thus as the heart's hemodynamics improves, IMD will continue to set new optimization curves to base the optimization therapy upon.

Thus, embodiments of the MEASUREMENT OF CORONARY SINUS PARAMETERS TO OPTIMIZE LEFT VENTRICULAR PERFORMANCE are disclosed. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. A method for pacing a patient's heart using an implanted medical device comprising:
   sensing a rate extraction of glucose through a coronary sinus of a patient's heart;
   generating pacing pulses as a function of the sensed rate;
   adjusting a pacing parameter of the pacing pulses as a function of a glucose signal; and
   adjusting the pacing parameter to optimize left ventricular performance wherein adjusting the pacing parameter comprises adjusting the pacing parameter to minimize the rate of extraction of glucose.

2. A method according to claim 1 wherein generating the pacing pulses comprises generating ventricular pacing pulses after expirations of AV intervals and wherein adjusting the pacing parameter comprises adjusting the AV intervals.

3. A method according to claim 1 wherein generating the pacing pulses comprises generating left and right ventricular pacing pulses separated by inter-ventricular VV intervals and wherein adjusting the pacing parameter comprises adjusting the inter-ventricular VV intervals.

4. A method according to claim 1 wherein adjusting the pacing parameter comprises setting a curve relating the pacing parameter to the rate of extraction of glucose.

5. A method according to claim 4 wherein adjusting the pacing parameter further comprises defining a region associated with the curve.

6. A method according to claim 5 further comprising resetting the curve responsive to the relationship of the pacing parameter and the sensed rate of extraction of glucose to the region.

7. A method for pacing a patient's heart using an implanted medical device comprising:
   sensing a rate extraction of glucose through a coronary sinus of a patient's heart;
   generating pacing pulses as a function of the sensed rate;
   adjusting a pacing parameter of the pacing pulses as a function of a glucose signal; and
   adjusting the pacing parameter to optimize left ventricular performance wherein adjusting the pacing parameter comprises setting a curve relating the pacing parameter to the rate of extraction of glucose.

8. A method according to claim 7 wherein adjusting the pacing parameter further comprises defining a region associated with the curve.

9. A method according to claim 8 further comprising resetting the curve responsive to the relationship of the pacing parameter and the sensed rate of extraction of glucose to the region.

10. A method according to claim 8 further comprising shifting the curve responsive to the relationship of the pacing parameter and the sensed rate of extraction of glucose to the region.

* * * * *